United States Patent [19]
Carpino et al.

[11] Patent Number: 6,040,422
[45] Date of Patent: Mar. 21, 2000

[54] SYNTHESIS AND USE OF AMINO ACID FLUORIDES AS PEPTIDE COUPLING REAGENT

[75] Inventors: Louis A. Carpino; Ayman Ahmed El-Faham, both of Amherst, Mass.

[73] Assignee: Research Corporation Technologies, Inc., Tucson, Ariz.

[21] Appl. No.: 09/002,860

[22] Filed: Jan. 5, 1998

Related U.S. Application Data

[62] Division of application No. 08/466,319, Jun. 6, 1995, Pat. No. 5,750,767, which is a continuation of application No. 08/284,964, Aug. 2, 1994, Pat. No. 5,712,418, which is a continuation-in-part of application No. 07/426,121, Oct. 23, 1989, Pat. No. 5,360,928.

[51] Int. Cl.$^7$ ..................................................... C07K 1/08
[52] U.S. Cl. ........................ 530/333; 564/225; 546/186; 560/161; 548/347
[58] Field of Search ........................... 564/225; 530/333; 546/186; 560/161; 548/347

[56] References Cited

U.S. PATENT DOCUMENTS

| | | | |
|---|---|---|---|
| 4,185,156 | 1/1980 | Umezawa et al. | 562/440 |
| 4,565,877 | 1/1986 | Wada et al. | 548/530 |
| 4,575,541 | 3/1986 | Carpino et al. | 525/333.5 |
| 4,743,612 | 5/1988 | Erhardt et al. | 514/392 |
| 5,360,928 | 11/1994 | Carpino | 562/849 |
| 5,712,418 | 1/1998 | Carpino | 564/225 |
| 5,750,767 | 5/1998 | Carpino | 560/161 |

FOREIGN PATENT DOCUMENTS

| | | |
|---|---|---|
| 0 075 434 | 3/1983 | European Pat. Off. . |
| WO 91/05564 | 5/1991 | WIPO . |
| WO 92/03409 | 3/1992 | WIPO . |
| WO 94/07910 | 4/1994 | WIPO . |

OTHER PUBLICATIONS

Beecham, "Tosyl-α-amino Acids", II. The Use of Acid Chlorides For Peptide Synthesis in the Presence of Aqueous Alkali, *J. Am. Chem. Soc.*, 79: 3262–3263 1957.

Beecham, "Tosyl-α-amino Acids," I. Degradation of the Acid Chlorides and Azides by Aqueous Alkali. *J. Am. Chem. Soc.*, vol. 79, 3257–3261, 1957.

Beyermann, et al., "Use of FMOC Amino Acid Chlorides in the Synthesis of Techykinin Sequences and Investigation of Their Histamine Releasing Activity", *Peptides*, pp. 107–110, 1986.

Beyermann, et al., "Rapid Continuous Peptide Synthesis via FMOC Amino Acid Chloride Coupling and 4-(Aminomethyl)piperidine Deblocking", *J. Org. Chem.*, 55, 721–728, 1990.

Carpino, et al., "((9–Fluorenylmethyl) oxy) carbonyl (FMOC Amino Acid Fluorides", *J. Am. Chem. Soc.*, 112, 9651–9652, 1990.

Carpino, et al., "tert–Butyloxycarbonyl and Benzyloxycarbonyl Amino Acid Fluorides", *J. Org. Chem.*, 56, 2611–2614, 1991.

Carpino, et al., "((9–Fluorenylmethyl)oxy)carbonyl Amino Acid Chlorides in Solid–Phase Peptide Synthesis," *J. Org. Chem.*, 56, 2635–2642, 1991.

Carpino, et al., "Protected β– and γ–Aspartic and –Glutamic Acid Fluorides", *J. Org. Chem.*, 57, 6371–6373, 1992.

Carpino, et al., "1–Hydroxy–7–azabenzotriazole," *J. Am. Chem. Soc.*, 115, 4397–4398, 1993.

Carpino, et al., "Tris (2–aminoethyl) amine as a Substitute for 4-(Aminomethyl) piperidine in the FMOC/Polyamine Approach to Rapid Peptide Synthesis", *J. Org. Chem.*, 55, 1673–1675, 1990.

Carpino, et al., "( (9–Fluorenylmethyl)oxy)carbonyl (FMOC) Amino Acid Chlorides," *J. Org. Chem.*, 51, 3732–3734, 1986.

Carpino, et al., "( (9–Fluorenylmethyl)oxy)carbonyl (FMOC) Amino Acid Fluorides", *J. Am. Chem. Soc.*, 112, 9651–9652, 1990.

Carter, et al., "The Acid Halides of p–Toluenesulfonyl–, Carbobenzoxy–, and Benzoyl–p–Methoxyphenyl–L–Alanine", *J. Biol. Chem.*, 178, 403, 409, 413, 1949.

Chemical Abstracts, 1984, 100: 103899.
Chemical Abstracts, 1984, 101: 110817h.
Chemical Abstracts, 1985, 102: 25040A.
Chemical Abstracts, 1995, 123: 33634w.

Coste, et al., "BROP: A New Reagent for Coupling N–Methylated Amino Acids," *Tetrahedron Lett.*, vol. 31, No. 5, pp. 669–672, 1990.

Coste, et al., "Oxybenzotriazole Free Peptide Coupling Reagents for N–Methylated Amino Acids", *Tetrahedron Letters*, vol. 32, No. 17, pp. 1967–1970, 1991.

(List continued on next page.)

*Primary Examiner*—Cecilia J. Tsang
*Assistant Examiner*—David Lukton
*Attorney, Agent, or Firm*—Scully, Scott, Murphy & Presser

[57] ABSTRACT

The present invention is directed to a process for forming a peptide bond between a first amino acid having a free amino group and a protected carboxy group and a second amino acid or between a peptide having a free amino group and a blocking carboxy group with a second amino acid which comprises (a) reacting the second amino acid of the formula:

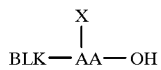

with a fluoroformamidinium salt of the formula:

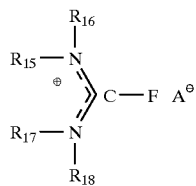

and (b) reacting the product of (a) with the first amino acid or peptide.

23 Claims, No Drawings

OTHER PUBLICATIONS

Dourtoglou, et al. "O–Benzotriazolyl–N,N,N',N'– tetramethyluronium Hexafluorophosphate as Coupling Reagent for the Synthesis of Peptides of Biological Interest", *Synthesis*, 572, 1984.

Green, "Solid–phase synthesis of [Ala$^{1,3,11,15}$] –endothelin–1 by a modified double–coupling procedure", *Int. J. of Peptide and Protein Research*, 41, 492–498, 1993.

Jakubke, et al., *Amino Acids, Peptides and Proteins*, 85, 88, 1962.

Jones, et al., "The Formation of 2–Benzyloxyoxazol–5–(4H)–ones from Benzyloxycarbonyl-l-amino acids", *J. Chem. Soc.*, 1979, 3202.

Jung, et al., "Synthesis and Structure–Activity Relationships of New Cephalosporins with Aminoimidazoles at C–7 effect of the pka of the c–7 Aminoimidazole on Antibacterial Spectrum and β– Lactamas Stability", *The Journal of Antibiotics*, pp. 992–1012, 1993.

Kirk, et al., "Photochemical Decomposition of Diazonium Fluoreborates," *J. of the Am. Chem. Soc.*, vol. 93, pp. 3060–3061.

Mobashery, et al., "A New Approach to the Preparation of N–Carboxy α–Amino Acid Anhydrides", *J. Org. Chem.*, 50, 2220–2202, 1985.

Mukaiyama, et al., "New Synthetic Reactions Based on the Onium Salts of Aza–Arenes", *Angew. Chem. I.E. Eng.*, 18, 707, 1979.

Wenschuh, et al., "Peptide Assembly in the Absence of Base via FMOC Amino Acid Fluorides", *J. Chem. Soc.,* pp. 669–670, 1995.

Wenschuh, et al., "Efficient Solid Phase Assembly of Peptides Bearing Contiguous Highly Hindered Aib Residues via FMOC Aib Fluoride," *Tetrahedron Letters*, vol. 34, No. 23, pp. 3733–3736, 1993.

Wiley, et al., "Base–catalyzed Decomposition of α–(Benzene–and p–Toluenesulfonamido) –phenylacetyl chlorides", *J. Am. Chem. Soc.*, 74, 936–938, 1952.

Wiley, et al., Decarboxylation of α–(Benzenesulfonamido)–carboxylic Acids, *J. Am. Chem. Soc.*, 73, 4719–4720, 1951.

Yamada, et al., "Studies of Separation of Peptide Diastereomers by Reversed–Phase HPLC and Its Applications," *Mem. Konan Univ. Sci. Ser.*, 32, 11, 1985.

SYNTHESIS AND USE OF AMINO ACID FLUORIDES AS PEPTIDE COUPLING REAGENT

RELATED APPLICATIONS

This is a divisional application of application Ser. No. 08/466,319, filed Jun. 6, 1995, now U.S. Pat. No. 5,750,767 which is a continuation of application, Ser. No. 08/284,964 filed Aug. 2, 1994, now U.S. Pat. No. 5,712,418 which is a continuation-in-part of application Ser. No. 426,121, filed on Oct. 23, 1989, now U.S. Pat. No. 5,360,928.

GOVERNMENT SPONSORSHIP

This work has been supported by a grant from the National-Institutes of Health and a grant from the National Science Foundation.

BACKGROUND OF THE DISCLOSURE

1. Field of the Invention

The present invention relates to novel amino acid fluorides and protected amino acid fluorides and their use in synthetic biochemistry, including peptide syntheses. More particularly, this invention is directed to the N-protected amino acid fluorides, and free amino acid fluorides and the hydrogen fluoride salts thereof, the side chain of which may be unprotected or protected with a blocking group and their use thereof in peptide synthesis.

2. Background of the Prior Art

As more and more polypeptides become of medicinal importance, there is an increasing incentive to improve the methods by which they may be synthesized. In recent years, peptides which have been found to be of possible pharmacological importance include those active against various diseases, such as cancers, diabetes, and plant toxins, etc. Others have shown specific activity as growth promoters or suppressants, antibiotics, insecticides, contraceptives, antihypertensives, sleep-inducers, anti-depressants, analgesics, etc. The list is long and varied.

Currently, syntheses of peptides in solution by classic or various repetitive methods or on a solid support (Merrifield) are popular techniques. Solution methods have the advantages of being easily monitored and allowing purification of intermediates, if necessary, at any stage. A major drawback is the relative slow pace of the synthesis with each step being carried out manually.

The major advantage of the Merrifield Method is its easy automation so that unattended, computer-controlled machine synthesis is possible. Unfortunately, this method suffers from an inherent deficiency due to the insoluble nature of the support on which the synthesis proceeds. Unless each acylation step occurs with 100% efficiency, mixtures will inevitably be built up on the polymer. The longer the chain, the greater will be the contamination due to undesired side reactions. Products produced in such reactions remain to contaminate the desired product when at the end of the cycle it is removed from the polymeric matrix. The properties of these peptides will not differ sufficiently for peptides of greater than about 30–40 residues to make efficient separation feasible.

For very long segments (50 or more amino acids), therefore, current methods are not satisfactory. Often mixtures are obtained of such forbidding complexity that it may be difficult or impossible to isolate the desired peptide.

The problems enumerated hereinabove could be eliminated if the proper derivatives of the underlying amino acids and the proper reaction conditions could be found.

For example, FMOC, (N$\alpha$-(9-fluorenylmethyl)-oxycarbonyl), protected amino acid chlorides, which are described by Carpino, et al. in *J. Org. Chem.* 51, 3732 (1986) have been used as acylating agents for stepwise peptide syntheses for both solution and solid phase techniques.

However, the amino acid chlorides have major drawbacks associated therewith. First, the acid chlorides react with trace amounts of water, such as moisture in the air, to give the corresponding amino acid. Therefore, they are not so stable, and as such, they are not a prime candidate for long term storage. Consequently, an objective was to find an amino acid derivative which was stable to moisture.

Moreover, another problem associated with amino acid chlorides is that it has not been possible to date to synthesize amino acid chlorides in which the protecting groups on the side chains of the amino acids can be removed under extremely mild conditions. As one skilled in the art is well aware, many of the amino acids have functional groups on the side chains which can interfere with peptide formation unless otherwise protected. In peptide synthesis, only the mildest conditions should be used to remove these protecting groups. For example, one of the easiest protecting groups to remove from the side chains containing amino, hydroxyl or carboxyl functions, such as lysine, tyrosine, threonine, serine, aspartic acid, glutamic acid and the like, is t-butyl or t-butyl containing moieties. For example, trifluoracetic acid can easily remove the t-butyl group from a serine side chain; on the other hand, a benzyl protecting group on the side chain can not be removed by said treatment but instead requires a more potent acid such as HF or trifluoromethanesulfonic acid. Therefore, the conditions for removing the benzyl group from the side chain are much harsher relative to the t-butyl groups. Furthermore, the mild catalytic hydrogenolysis of benzyl groups is not generally applicable to long chain peptides or resin attached peptides.

Although benzyl groups on the side chains of N-protected amino acid chlorides, can be prepare, such as FMOC-cysteine-S-benzyl chloride, FMOC-lysine-$\epsilon$ carbobenzoxy chloride, FMOC-tyrosine-O-benzyl chloride, FMOC-serine-O-benzyl chloride and FMOC aspartic acid $\beta$-benzyl ester, these molecules suffer from the disadvantages described hereinabove. Consequently, an investigation was commenced to determine if t-butyl or "t-butyl like" containing groups can be used to protect the side chain of amino acid chlorides. Unfortunately, efforts in this area were unsuccessful. None of the above compounds could be synthesized if the t-butyl group was used in place of the benzyl substitution.

This was not unusual since it is well known that t-butyl-based protecting groups are readily deblocked by hydrogen chloride which is an inevitable by-product of acid chloride formation and/or long term storage (hydrolysis by trace amounts of water). For example, in the case of the FMOC-tyrosine derivative 1, the acid chloride could be obtained, but after several days it was noted to lose the t-butyl group slowly.

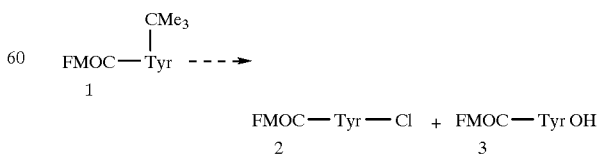

Furthermore, compound 1 as well as the analogous serine and threonine derivatives could be obtained only as oils which could not be crystallized and were therefore difficult, if not impossible, to purify.

In the case of the FMOC aspartic acid derivative 4, treatment with thionyl chloride gave only the aspartic acid anhydride 6, presumably via the unstable acid chloride 5 which undergoes intramolecular loss of t-butyl chloride.

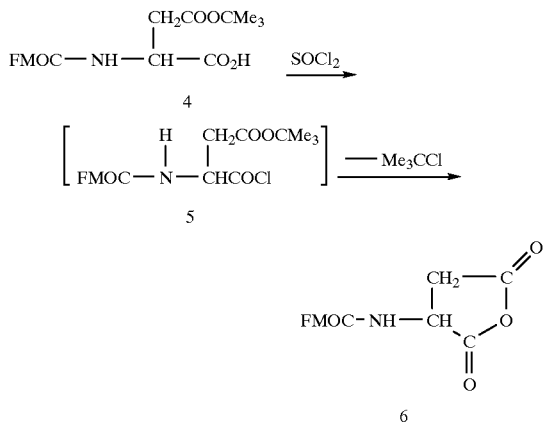

Lysine derivative 7 could not be converted to an acid chloride because of the marked sensitivity of the BOC function.

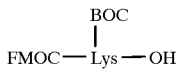

Similar problems arise in the cases of Arg, His, Asn, Gln, and Trp. The net result of these problems is that only about one half of the commonly occurring amino acids can be converted to stable amino acid chlorides.

Therefore, a search was undertaken to find an amino acid candidate for use in peptide synthesis which is inexpensive, stable to moisture, and which shows great potential for long-term storage. Moreover, it was hoped that a candidate could be found where the protecting groups on the amino acid side chain could be removed under milder conditions then those used to remove the benzyl group. Preferably, it was hoped that a t-butyl containing group or a group as easily removable as t-butyl could be placed on the side chain of these amino acid candidates.

The present invention circumvents the difficulties experienced with respect to the acid chlorides and accomplishes the goals described hereinabove. The compounds of the present invention are effective in coupling with amino acids or peptides to form new peptide bonds. Moreover, the compounds of the present invention are more stable to moisture then the acid chlorides and therefore can be used for long term storage. Furthermore, t-butyl containing protecting groups and other protecting groups can be placed on the side chains of these amino acid compounds and removed under milder conditions than those required for the removal of benzyl groups. Finally, the compounds of the present invention are potent acylating agents in peptide bond formation.

These compounds are, much to our surprise, the corresponding amino acid fluorides.

SUMMARY OF THE INVENTION

The present invention is directed to an amino acid of the formula:

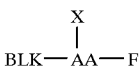

or the hydrogen fluoride salts thereof wherein
BLK is an N-amino protecting group;
AA is an amino acid residue; and
X is - or a protecting group.

The present invention is also directed to a method for preparing a peptide which comprises reacting the amino acid fluoride described hereinabove with an amino acid or peptide having a free amino group and removing the protecting groups therefrom.

In addition, the present invention is directed to a method for preparing amino acid fluorides using a new fluorinating agent, a fluoroformamidinium salt, of the formula:

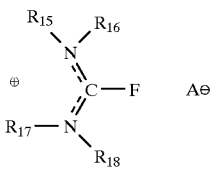

wherein $R_{15}$, $R_{16}$, $R_{17}$ and $R_{18}$ are independently lower alkyl, aryl, aryl lower alkyl, cycloalkyl, cycloalkyl lower alkyl or $R_{15}$ and $R_{16}$ taken together with the nitrogen atom to which they are attached form a 5- or 6-membered ring or $R_{17}$ and $R_{18}$ taken together with the nitrogen atom to which they are attached form a 5- or 6-membered ring or $R_{15}$, $R_{16}$, $R_{17}$ and $R_{18}$ taken together with the nitrogen atom to which they are attached form a 5- or 6-membered ring and $A^-$ is a counter ion.

The present invention is also directed to use of the fluoroformamidinium agent as a coupling agent for the assembly of peptides.

DETAILED DESCRIPTION OF THE INVENTION

As used herein, the term "amino acid" refers to an organic acid containing both a basic amino group ($NH_2$) and an acidic carboxyl group (COOH). Therefore, said molecule is amphoteric and exists in aqueous solution as dipole ions. (See, "The Condensed Chemical Dictionary", 10th ed. edited by Gessner G. Hawly, Van Nostrand Reinhold Company, London, Eng. p.48 (1981)). The preferred amino acids are the α-amino acids. They include but are not limited to the 25 amino acids that have been established as protein constituents. They must contain at least one carboxyl group and one primary or secondary amino group on the amino acid molecule. They include such proteinogenic amino acids as alanine, valine, leucine, isoleucine, norleucine, proline, hydroxyproline, phenylalanine, tryptophan, methionine, glycine, serine, threonine, cysteine, cystine, tyrosine, asparagine, glutamine, aspartic acid, glutamic acid, lysine, hydroxylysine, ornithine, arginine, histidine, penicillamine and the like.

An "amino acid residue", as defined herein, is an amino acid minus an amine hydrogen on the amino end of the molecule and the OH group on the carboxy end of the molecule (i.e., it includes the acyl group on the carboxy end of the molecule). Therefore, unless designated to the contrary, the group "AA" signifies an amino acid residue. For example, the amino acid residues of various amino acids are represented below:

| AA Symbol | AA Residue |
|---|---|
| Gly | —NH—CH$_2$—C(=O)— |
| Ala | —NH—CH(CH$_3$)—C(=O)— |
| Leu | —NH—CH(CH$_2$CH(CH$_3$)$_2$)—C(=O)— |
| Ile | —NH—CH(CH(CH$_3$)CH$_2$CH$_3$)—C(=O)— |
| Pro | (pyrrolidine ring)—C(=O)— |
| Phe | —NH—CH(CH$_2$C$_6$H$_5$)—C(=O)— |
| Trp | —HN—CH(CH$_2$-indole)—C(=O)— |
| Met | —HN—CH((CH$_2$)S—CH$_3$)—C(=O)— |
| Ser | —HN—CH(CH$_2$OH)—C(=O)— |

-continued

| AA Symbol | AA Residue |
|---|---|
| Thr | —HN—CH(CH(OH)CH$_3$)—C(=O)— |
| Cys | —HN—CH(CH$_2$SH)—C(=O)— |
| Tyr | —HN—CH(CH$_2$-C$_6$H$_4$-OH)—C(=O)— |
| Asn | —NH—CH(CH$_2$CONH$_2$)—C(=O)— |
| Gln | —HN—CH((CH$_2$)CONH$_2$)—C(=O)— |
| Asp | —HN—CH(CH$_2$COOH)—C(=O)— |
| Glu | —HN—CH((CH$_2$)$_2$COOH)—C(=O)— |
| Lys | —HN—CH((CH$_2$)$_4$NH$_2$)—C(=O)— |
| Arg | HN—CH(CH$_2$CH$_2$CH$_2$NH—C(=NH)—NH$_2$)—C(=O)— |

-continued

| AA Symbol | AA Residue |
|---|---|
| His | —HN—CH—C—<br>         \|        ‖<br>         CH₂—C=CH  O<br>                \|    \|<br>                N   NH<br>                  \\ /<br>                   CH |
| Nor | —HN—CH—C—<br>         \|      ‖<br>         (CH₂)₂ O<br>         \|<br>         CH₃ |

Therefore, the symbol "AA-F" refers to an amino acid fluoride, i.e., a compound having a fluoro group attached to the acyl group

of the amino acid. When BLK is hydrogen, then the structure becomes the amino acid fluoride of an amino acid having a free amino group. However, in view of the synthesis of the amino acid fluoride described hereinbelow, the free amino acid fluoride may be isolated as the hydrogen fluoride salt thereof.

It will be apparent to one skilled in the art, shown by exemplification in the table hereinabove that in the course of protein synthesis, it may be necessary to protect certain side chains of the amino acids to prevent unwanted side reactions. For example, it may be necessary to protect the hydroxyl group on the side chain of tyrosine, serine, or threonine in order to prevent these groups from interfering with the desired reactions. This is a common problem in peptide synthesis and many procedures are available for protecting the functional groups on the side chains of the amino acids. Such procedures for protecting various functional groups are known to one skilled in the art and are described in the treatise entitled "The PEPTIDES", Vol. 2, Edited by E. Gross and J. Meienhoffer, Academic Press, New York, N.Y., pp. 166–251 (1980), and the book entitled "Reagents for Organic Synthesis", by T. W. Green, John Wiley and Sons, New York, 1981, the contents of both being incorporated herein by reference.

For example, when the functional side chain contains an hydroxy group, such as threonine or serine, it can be protected by such groups as methyl, methoxymethyl (MOM), 2-methoxyethoxymethyl(MEM), tetrahydropyranyl, β-trimethylsilylethyl, 4-methoxytetrahydropryanyl, 1-ethoxyethyl, t-butyl, p-methoxybenzyl, p-halobenzyl, o-nitrobenzyl, p-nitrobenzyl, o-chlorobenzyl, adamantyl, diphenylmethyl, triphenylmethyl, cyclohexyl, cyclopentyl, 1-benzyloxymethyl, tri-substituted silyl, wherein the substituents are independently aryl, alkyl or aralkyl, 2,2,2-trifluoroethyl, and the like. The preferred groups for the protection of the hydroxyl side chain are adamantyl, t-butyl, 4-methoxybenzyl, cyclopentyl and cyclohexyl.

When the side chain contains a phenol, such as in tyrosine, it may be protected by such groups as methyl, methoxymethyl(MOM), methoxyethoxymethyl(MEM), B-trimethylsilylethyl, methylthiomethyl, tetrahydropyranyl, isopropyl, cyclohexyl, cyclopentyl, t-butyl, adamantyl, 4-methoxyphenylsilyl, o-nitrobenzyl, 2,4-dinitrophenyl, m-bromobenzyl, 2,6-dichlorobenzyl, trisubstituted-silyl wherein the substituents are independently alkyl, aryl or aralkyl, ethoxycarbonyl, carbamoyl and the like. The most preferred protecting groups are adamantyl, 4-methoxybenzyl, t-butyl, cyclopentyl, and cyclohexyl. An especially preferred protecting group is t-butyl.

A carboxy side chain, such as that found in aspartic acid or glutamic acid, can be protected by the following groups: 1-or 2-adamantyl, methoxymethyl, methythiomethyl, t-butyl, methyl, ethyl, phenyl, tetrahydropyranyl, cyclopentyl, cyclohexyl, cycloheptyl, 4-picolyl, trisubstituted-silyl wherein the substituents are independently alkyl, aryl or aralykl, N-piperidinyl, N-succinimidoyl, β-trimethylsilylethyl, 4-methoxybenzyl, benzyl, p-bromobenzyl, p-chlorobenzyl, p-nitrobenzyl, phenacyl, N-phthalimidoyl, 4-alkyl-5-oxo-1,3-oxazolidinyl, trisubstituted-stannyl wherein the substituents are independently alkyl, aryl or aralkyl, and the like. The most preferred protecting group is t-butyl.

If the functional group on the side chain is mercapto, e.g., cysteine, such groups as triphenylmethyl, benzyl, 4-methylbenzyl, 3,4-dimethylbenzyl, 4-methoxybenzyl, β-trimethylsilylethyl, p-nitrobenzyl, 4-picolyl, diphenylmethyl, triphenylmethyl, bis(4-methoxyphenyl) methyl, diphenyl-4-pyridylmethyl, 2,4-dinitrophenyl, t-butyl, t-butylthio, adamantyl, isobutoxymethyl, benzylthiomethyl, thiazolidinyl, acetamidomethyl, benzamidomethyl, 2-nitro-1-phenylethyl, 2,2-bis (carboethoxy)ethyl, 9-fluorenemethyl, acetyl, benzoyl, and the like can be used to protect said group. In this case, it is preferred that the protecting groups are t-butyl, t-butylthio, 4- methoxybenzyl, and triphenylmethyl.

If the side chain contains an amino group, such as the ε-amino group of lysine and ornithine, the following groups may be used: 9-fluorenyl-methyloxycarbonyl, 9-(2-sulfo) fluorenylmethyloxycarbonyl, β-trimethylsilyl ethyloxycarbonyl, 2-furanylmethyloxycarbonyl, adamantyloxycarbonyl, carbobenzoxy, t-butyloxycarbonyl, t-amyloxycarbonyl, cyclobutyloxycarbonyl, 1-methylcyclobutyloxycarbonyl, cyclopentyloxycarbonyl, cyclohexyloxycarbonyl, 1-methylcyclohexyloxycarbonyl, isobornyloxycarbonyl, benzyl, p-methoxybenzyloxycarbonyl, p-nitrobenzyloxycarbonyl, chlorobenzyloxycarbonyl, isonicotinyloxycarbonyl, p-toluenesulfonylamidocarbonyl, methylsulfonylethyloxycarbonyl, β,β,β-trichloro-ethyloxycarbonyl, dithiasuccinoyl, phthaloyl, 4,5-diphenyl-4-oxazoline-2-one, piperidino oxycarbonyl trifluoroacetyl, chloroacetyl, p-toluenesulfonyl and the like. Preferred groups for the protection of this amino side chain are carbobenzoxycarbonyl, t-butyloxycarbonyl, and adamantyloxycarbonyl.

If the amino acid has an imidazole group, such as in histidine, the following groups may be used to protect the side chain: benzyloxymethyl, piperdinylcarbonyl, phenacyl, pivaloyloxymethyl, 1-(alkoxycarbonylamino)-2,2,2-trifluoroethyl, 1-trifluoromethyl-1-(p-chlorophenoxy-methoxy)-2,2,2-trifluoroethyl, 2,4-dinitrophenyl, toluenesulfonyl, FMOC, triphenylmethyl, t-butyloxycarbonyl, t-butyloxymethyl and the like. The preferred groups are FMOC, t-butyloxycarbonyl, triphenylmethyl, and t-butyloxymethyl.

When the amino acid has a guanidine side chain, such as in arginine, the following protecting groups can be used to protect the ω-nitrogen on the guanidine moiety: methoxytrimethylbenzenesulfonyl, pentamethylchromanesulfonyl, mesitylenesulfonyl, tolunesulfonyl, 2,4,6-trimethylbenzenesulfonyl, trimethoxybenzensulfonyl, bisadamantyloxylcarbonyl, nitro, tosyl, and the like. The preferred protecting groups are methoxytri-methylsulfonyl, pentaamethylchromanesulfonyl, bisadamantyloxycarbonyl, and mesitylenesulfonyl.

For side chains containing an amide group such as in glutamine and asparagine, the following groups can be used to protect the side chain: dimethoxybenzyhydryl, 9-xanthenyl, 2,4,6-trimethoxybenzyl, and the like.

As used herein in the instant specification, the term "alkyl", when used alone or in combination with other groups refers to a carbon chain containing from 1 to 6 carbon atoms. They may be straight chains or branched and include such groups as methyl, ethyl, propyl, isopropyl, n-butyl, sec-butyl, isobutyl, t-butyl, n-pentyl, amyl, n-hexyl and the like. The preferred alkyl group contains from 1–3 carbon atoms. The term aryl as used herein refers to an aromatic ring system containing from 6–10 ring carbon atoms and up to a total of 15 carbon atoms. It includes such groups as phenyl, α-naphthyl, β-naphthyl, and the like. The preferred group is phenyl.

Aralkyl groups are aryl groups attached to the main chain through an alkylene bridge. Such groups include benzyl, phenethyl and the like. The preferred aralkyl group is benzyl.

The aryl and aralkyl groups herein may be unsubstituted or may be substituted with an electron donating group in situations wherein the protecting group is cleaved by acid. An electron donating group as defined herein shall be interpreted as a group that will release or donate electrons more than hydrogen would if it occupied the same position in the molecule. See, J. Marsh, Advance Organic Chemistry, 2nd Ed., McGraw Hill, Inc. (1977). These types of groups are well known in the art. Examples of electron donating groups include alkyl, lower alkoxy, aralkoxy; and the like. These electron donating groups, e.g., alkoxy, may be present on the aryl moiety of the following groups: DMB, TMB, Mtr, Pmc, Bz, Trt, CBZ and the like.

The protecting groups described hereinabove are well known to one skilled in the art. They can be removed under very mild acidic or basic conditions. The preferred protecting groups are those which can be cleaved by acid or base under conditions which are milder than those used to cleave the benzyl group. These include groups which can be cleaved by trifluoroacetic acid at room temperature within one to four hours. The especially preferred protecting groups are groups which can be cleaved by trifluoroacetic acid at room temperature within 1–2 hours.

These protecting groups include such groups as tetrahydropyranyl, β-trimethylsilylethyl, 1-ethoxyethyl, t-butyl, p-methoxybenzyl, 1-adamantyl, diphenylmethyl, triphenylmethyl, trialkylsilyl, (e.g. tri-methylsilyl, triethylsilyl, and the like) trialkylstannyl, (e.g. trimethylstannyl, triethylstannyl, and the like), bis(4-methoxyphenyl)methyl, 2-furanylmethyloxycarbonyl, t-amyl-oxycarbonyl, 1-methylcyclohexyloxycarbonyl, isobornyloxy carbonyl, methoxytrimethylbenzenesulfonyl, pentamethylchromanesulfonyl, 2,4,6-trimethoxybenzyl, 9-xantheneyl and the like.

However, not all of the amino acids have side-chain functional groups. For example, many amino acids have hydrogen, alkyl or aralkyl side chains. These include glycine, alanine, valine leucine, norleucine, phenylalanine, isoleucine and the like. Therefore, these amino acids do not require protecting groups thereon.

To differentiate between those amino acids having protecting groups and those not having protecting groups thereon, the term

X
|
AA is used. As used herein, if no protecting group is present on the amino acid side chain, such as, e.g., in alanine, (which doesn't have a functional group and therefore no blocking group is required) "X" is -. Moreover, if the amino acid side chain has a functional group, such as in tyrosine, but is unprotected, then this also is indicated by X being defined as -. In other words, in both instances, when X is -, the side group is unprotected.

Although the term functional group is understood by one skilled in the art, it is defined as a group which could react with the reactants used or products formed under peptide forming condition if not protected by a blocking group. These functional groups include amino, carboxy, hydroxy, guanidine, imidazole, amino and the like.

On the other hand, if X is a blocking group, then this signifies that the functional group on the side chain is protected. For example, if AA is serine and X is t-butyl, then the residue

X
|
"AA"

becomes

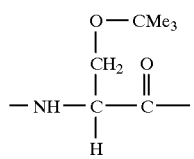

$$\begin{array}{c} \text{O}-\text{CMe}_3 \\ | \\ \text{CH}_2 \quad \text{O} \\ | \quad \| \\ -\text{NH}-\text{C}-\text{C}- \\ | \\ \text{H} \end{array}$$

These protecting groups include the protecting groups described hereinabove.

Abbreviations have been used in the specification and claims with respect to these blocking groups and are listed hereinbelow:

| Protecting group | Abbreviation |
|---|---|
| dimethoxybenzhydryl | DMB |
| 2,4,6-trimethoxybenzyl | TMB |
| 2,3,6-trimethyl-4 methoxybenzenesulfonyl | Mtr |
| 9-fluorenylmethyloxycarbonyl | FMOC |
| t-butoxycarbonyl | BOC |
| t-butoxymethyl | Bom |
| pentamethylchromanesulfonyl | Pmc |
| adamantyl | ada |
| β-trimethylsilylethyl | TMSE |
| β-trimethylsilylethyloxycarbonyl | TEOC |
| t-butyl | t-bu |
| benzyl | Bz |
| cyclopentyl | Cp |
| cyclohexyl | Ch |
| triphenylmethyl | Trt |
| benzyloxycarbonyl | Cbz |
| adamantyloxycarbonyl | Adoc |
| formyl | CHO |
| trifluoroacetyl | TFA |

The term amino acid protecting group, as used herein, refers to blocking groups which are known in the art and which have been utilized to block the amino (NH$_2$) group of the amino acid. Blocking groups such as 9-lower alkyl-9-fluorenyloxycarbonyl,2-chloro-1-indanylmethoxycarbonyl (CLIMOC) and benz [f] indene-3-methyloxycarbonyl (BIMOC) and dbd-TMOC are discussed in U.S. Pat. Nos. 3,835,175, 4,508,657, 3,839,396, 4,581,167, 4,394,519, 4,460,501 and 4,108,846, and the contents thereof are incorporated herein by reference as is fully set forth herein. Moreover, other amino protecting groups such as 2-(t-butyl sulfonyl)-2-propenyloxycarbonyl (Bspoc) and benzothiophene sulfone-2-methyloxycarbonyl (Bsmoc) are discussed in U.S. Pat. No. 5,221,754 and the subject matter therein is incorporated herein by reference. Other amino protecting groups are described in an article entitled "Solid Phase Peptide Synthesis" by G. Barany and R. B. Merrifield in *Peptides,* Vol. 2, edited by E. Gross and J. Meienhoffer, Academic Press, New York, New York, pp. 100–118 (1980), the contents of which are incorporated herein by reference. These N-amino protecting groups include such groups as the FMOC, Bspoc, Bsmoc, t-butyloxycarbonyl (BOC), t-amyloxycarbonyl (Aoc), β-trimethylsilylethyloxycarbonyl (TEOC), adamantyloxycarbonyl (Adoc), 1-methylcyclobutyloxycarbonyl (Mcb), 2-(p-biphenylyl)propyl-2-oxycarbonyl (Bpoc), 2-(p-phenylazophenyl)propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), p-toluenesulfonyl aminocarbonyl (Tac) o-nitrophenylsulfenyl (Nps), dithiasuccinoyl (Dts), phthaloyl, piperidino- oxycarbonyl, formyl, trifluoroacetyl and the like.

These protecting groups can be placed into four categories:

1) a base labile Na-amino acid protecting group such as FMOC, and the like.

2) protecting groups removed by acid, such as Boc, TEOC, Aoc, Adoc, Mcb, Bpoc, Azoc, Ddz, Poc, Cbz, 2-furanmethyloxycarbonyl (Foc), p-methoxybenzyloxycarbonyl (Moz), Nps, and the like.

3) protecting groups removed by hydrogenation such as Dts, Cbz.

4) protecting groups removed by nucleophiles, such as Bspoc, Bsmoc and Nps and the like.

5) protecting groups derived from carboxylic acids, such as formyl, acetyl, trifluoroacetyl and the like, which are removed by acid, base or nucleophiles.

As defined herein, a nucleophile is an electron-rich atom, i.e., an atom which can donate an electron pair, which tends to attack a carbon nucleus but does not act as a Bronsted Lowry base. For example, a nucleophile, as defined herein, includes those molecules which are used for nucleophilic addition across a double bond and behaves in a manner similar to that described in the schemes herein below.

The general mechanism for cleavage of Bspoc and Bsmoc groups are similar in that the nucleophile is believed to react through a Michael-type addition across a double bond. Although the following schemes are shown for Bspoc, it is also illustrative of Bsmoc:

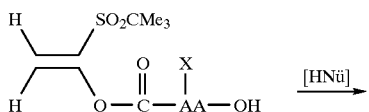

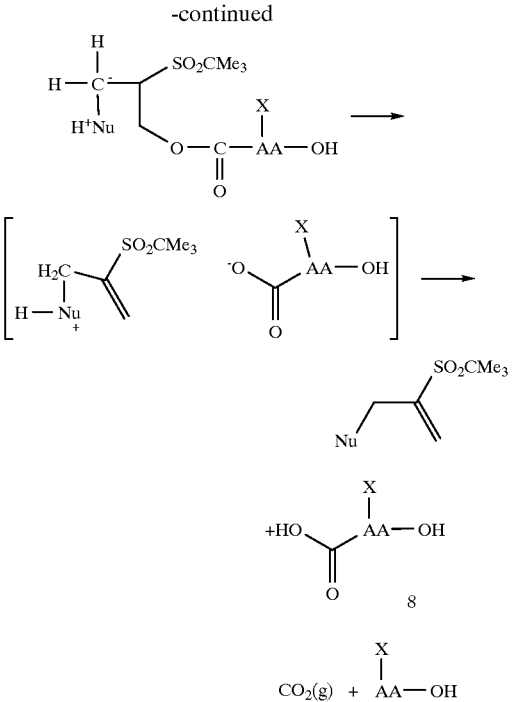

The nucleophile is believed to attack at the terminal carbon atoms of the propenyl group (Michael acceptor) forming a zwitterion which can eliminate the OCOAA(X)OH anion and H+ to form an alkene-amine and the carbamic acid (8) after protonation. Loss of CO$_2$ will furnish the free amino acid.

The nucleophiles which will function in concert with this invention must have an active hydrogen atom, i.e., a hydrogen atom attached to the nucleophilic atom.

It is preferred that the nucleophile is a simple amine. It is especially preferred that the simple amine is a primary or secondary amine of the formula HNR$_{19}$R$_{20}$ wherein R$_{19}$ and R$_{20}$ are independently hydrogen, lower alkyl or substituted lower alkyl, the lower alkyl being substituted with OH, CH$_3$, or CH$_2$CH$_3$ or R$_{19}$ and R$_{20}$ taken together form a mono or bicyclic ring containing from 4 to 10 ring carbon atoms and 1 or 2 heteroatoms selected from the group consisting of nitrogen, sulfur or oxygen.

Typical examples of useful amines include ethanolamine, morpholine, piperidine, diethylamine, 2,6-dimethylpiperidine, piperazine, diethylamine, ethylamine and the like.

An organo mercaptan can also be used as a nucleophile, e.g., alkyl mercaptans, cycloalkyl mercaptans, aryl mercaptan or aralkyl mercaptans. The most preferred mercaptan is benzyl mercaptan. However, when an organomercaptan is used as the nucleophile, the deblocking reaction additionally requires a base catalyst, such as, for example, triethylamine and the like.

The nucleophile can be added as a free compound or as an insoluble reagent attached to a solid support i.e., polystyrene or silica dioxide. These are represented by the formula:

p-[alk]-NuH wherein p is an organic polymer as defined hereinabove or a silica gel polymer; alk is a chemical bond, alkyl or aroyl chain having from about one to about ten carbon atoms and Nu-H is a nucleophile as defined hereinabove.

A preferred insoluble reagent is the silica based piperazine reagent 9:

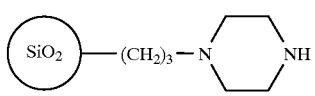

Another useful nucleophile is benzylmercaptan as shown in the following scheme.

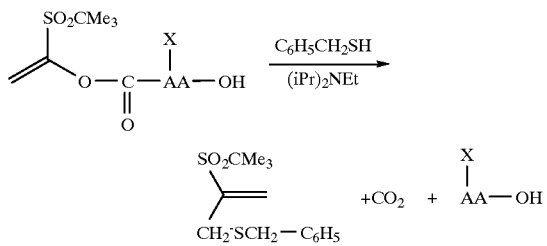

In this scheme the thio-group reacts in a Michael fashion to remove the Bspoc protecting group.

The amino acid fluorides of the present invention can be prepared by art recognized techniques. More specifically, they can be prepared by reacting an N-protected amino acid with the reagent cyanuric fluoride according to the following equation:

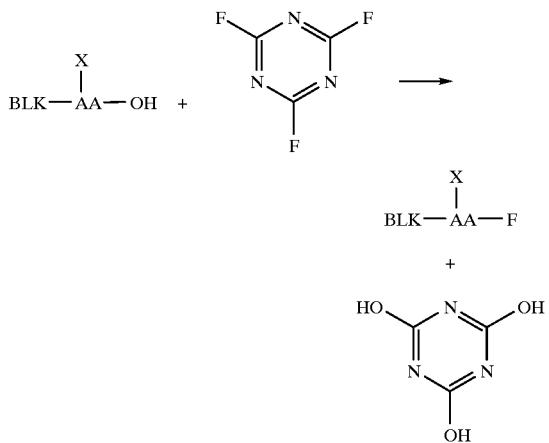

wherein BLK is an amino protecting group as defined herein and X is defined herein. It is preferred that BLK is the FMOC CLIMOC, BIMOC, DBD-TMOC, Bspoc, Bsmoc, or related base sensitive group. This reaction can be run at temperatures as low as 0° and up to the refluxing temperature of the solvent, but it is preferred that reaction is run at room temperature. It also can be run in an inert solvent such as pyridine/$CH_2Cl_2$ and the like.

The cyanuric fluoride can be prepared from the corresponding chloride in the presence of potassium fluoride at elevated temperatures ranging from 150° to 250° C., according to the following equation:

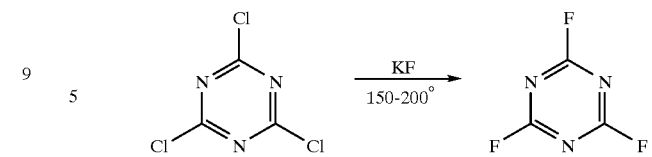

Other fluorinating agents well known in the art, such as thionyl fluoride, 2,4,6-trinitrofluorobenzene, N-methyl-2-fluoropyridinium salts, and the like may be used in place of KF to effect the formation of cyanuric fluoride.

Besides the methods described hereinabove, a new method has been developed to synthesize the protected amino acid fluorides of the instant specification. The new fluorinating agent is a fluoroformamidinium salt and has the formula:

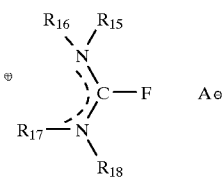

wherein $R_{15}$, $R_{16}$, $R_{17}$, and $R_{18}$ are independently lower alkyl or aryl, aryl lower alkyl, cycloalkyl, cylcoalkyl lower alkyl or $R_{15}$ and $R_{16}$ taken together with the nitrogen atom to which they are attached form a 5- or 6-membered ring or $R_{15}$, $R_{16}$, $R_{17}$ and $R_{18}$ taken together with the nitrogen atom to which they are attached form a 5- or 6-membered ring or $R_{15}$, $R_{16}$, $R_{17}$ and $R_{18}$ taken together with the nitrogen atom to which they are attached form a 5- or 6-membered ring and A is a counterion.

The aryl, arylalkyl and alkyl groups are as defined hereinabove.

The term "cycloalkyl" refers to a single ring or a fused ring system containing 3–10 ring carbon atoms and up to a total of 12 carbon atoms. The only ring atom in cycloalkyl are carbon atoms, i.e., there are no hetero ring atoms. The cycloalkyl group may be completely saturated or partially saturated. It may contain one ring or it can contain two, three or more rings. It is preferred that the cycloalkyl group be bicyclic and especially monocyclic. In addition, it is preferred that the ring contain 5–10 ring carbon atoms, especially, 5, 6 or 10 ring carbon atoms. Examples include cyclopropyl, cyclobutyl, cyclopentyl, cyclohexyl, cycloheptyl, cyclooctyl, adamantyl, decalinyl, indanyl, and the like. The preferred cycloalkyl groups are cyclopentyl and cyclohexyl.

Cycloloweralkyl is an alkylene group, as defined above, bridging the main chain with a cycloalkyl group, as defined herein. Examples include cyclopentylmethyl, cyclohexylmethyl, and the like.

A counterion, as used herein, is an anion used to neutralize the cationic portion of the molecule. Examples include hexafluorophosphate, halide, sulfate, $BF_4^-$, sulfite, nitrate, nitrite, acetate, phosphate, oleate, sulide, carboxylate, bisulfate, and the like.

Preferred values of $R_{15}$, $R_{16}$, $R_{17}$ and $R_{18}$ are lower alkyl and aryl. It is preferred that $R_{15}$, $R_{16}$, $R_{17}$ and $R_{18}$ are alkyl containing 1–3 carbon atoms, especially methyl or phenyl. It is preferred that at least two and more preferably, three of $R_{15}$, $R_{16}$ and $R_{17}$ are loweralkyl. Examples of the fluoroformamidinium salt of the present invention include tetramethyl fluoroformamidinium hexafluorophosphate (TFFH), trimethylphenylfluoroformamidinium hexafluorophosphate (TPFFH), and the like.

It is also preferred that $R_{17}$ and $R_{18}$ and/or $R_{15}$ and $R_{16}$ taken together with the nitrogen atom to which they are attached form a 5- or 6-membered ring, e.g., piperidine, pyrrolidine, and the like. It is even more preferred that both $R_{17}$ and $R_{18}$ taken together with the nitrogen atom to which they are attached and $R_{15}$ and $R_{16}$ taken together with the nitrogen atom to which they are attached form a 5- or 6-membered ring. In both instances, the rings may be unsubstituted or substituted with lower alkyl. It is even more preferred that the ring that is formed between $R_{15}$, $R_{16}$ and the nitrogen atom to which they are attached is the same and the ring formed between $R_{18}$ and $R_{17}$ and the nitrogen atom to which they are attached are the same. Examples thereof include bis(tetramethylene) fluoroformamidinium, hexafluorophosphate (BTFFH) and the like.

Another preferred embodiment of the present invention is when $R_{15}$, $R_{16}$, $R_{17}$ and $R_{18}$ taken together form a 5- or 6-membered ring, such as, for example, imidazolidine, hexahydropyrimidine, and the like, which may be unsubstituted or substituted with lower alkyl. An example thereof is 1, 3-dimethyl-2-fluoroimidazolium hexafluorophosphate (DFIH), and the like.

The fluoroformamidinium salts of the present invention are prepared in accordance with art recognized techniques. For example, the fluoroformamidinium salts can be prepared from reacting the corresponding chloride salt with a fluorinating agent such as a fluoride, (e.g., alkali fluoride, such as KF, NaF, and the like) or $PF_6^-$, and the like in a dry inert polar solvent, such as acetonitrile, and the like. The reaction can be effected at temperatures as low as 0° and up to the refluxing temperature of the solvent, but it is preferred that the reaction is run at room temperature.

The chloro derivatives can be prepared in accordance with art recognized techniques, such as the methodology described by Dourtaglou and Gross in *Synthesis* 572 (1984), the contents of which are incorporated by reference. For example, a urea derivative such as

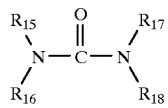

is reacted with a chlorinating agent phosgene or oxalyl chloride, and the like, which after $CO_2$ evolution, and addition of the counterion, affords the chloro formadinium salt, wherein $R_{15}$, $R_{16}$, $R_{17}$ and $R_{18}$ are as defined herein.

The fluoroformamidinium salt of the present invention, as indicated hereinabove, can also be used to synthesize the protected amino acid fluorides of the present invention. More specifically, the protected amino acid fluorides of the present invention can be prepared by reacting an N-protected amino acid with the fluoroformamidinium salt. This reaction is preferably run in an inert solvent, such as chloroform or methylene chloride. This reaction can be run at temperatures as low as 0° C. and up to the boiling point of the solvent, but it is preferred that the reaction is run at room temperature. Additionally, it is preferred that the reaction is run in the presence of a base, such as pyridine, triethylamine, and the like.

The amino acid fluorides of the present invention are useful in peptide bond formation. The scope is quite broad, as the amino acid fluorides of the present invention can be coupled with an amino acid, a dipeptide, tripeptide, or higher peptide, having a free terminal amino group. As used herein, the term first amino acid is meant to include amino acids as well as dipeptides, and the higher peptides.

The synthesis of peptides according to the present invention requires the following steps:

1) protection of the carboxyl group on a first amino acid.
2) formation of the amino acid fluorides of the present invention in accordance with the procedure herein.
3) formation of the peptide bond by coupling the amino acid fluoride with the first amino acid.
4) removal of the protecting groups.

A variety of carboxy protecting groups known in the art may be employed. Examples of many of these possible groups may be found in "Protective Groups in organic Synthesis", by T. W. Green, John Wiley & Sons, 1981, the contents of which is incorporated herein by reference.

The following sequence is illustrative of the coupling of an amino acid fluoride of the present invention with an amino acid having a free amino group:

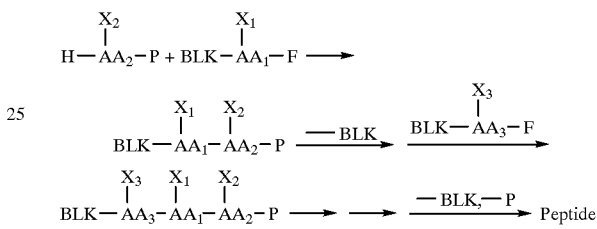

In the above scheme, BLK is as defined hereinabove, $X_1$, $X_2$ and $X_3$ are independently defined as X hereinabove, and P is a carboxy protecting group, e.g., methyl ester, t-butylester, β-trimethylsilylethyl ester, benzyl ester and the like.

As shown by the above scheme, the Nα-amino protected amino acid fluoride is reacted with a second amino acid in which the carboxy group is protected. A peptide is formed between the first amino acid and the second amino acid. The peptide chain can be increased by removing the alpha amino protecting group by techniques known to one skilled in the art, and then reacting the corresponding di-peptide with another Nα-amino protected amino acid fluoride to form the corresponding tri-peptide. The Nα-amino protecting group of the tri-peptide is removed and the above cycle is repeated until the desired peptide has been obtained.

The coupling of the N-α protected amino acid fluoride with the carboxy protected amino acid by the normal two phase technique takes place without racemization.

The present invention can readily be utilized in solid phase peptide synthesis. Solid phase peptide synthesis is based on the stepwise assembly of a peptide chain while it is attached at one end to a solid support or solid phase peptide resin. Two methods are generally well known in the art.

One, the Merrifield method, employs a solid support for attachment of the amino acid or peptide residues. This method employs N-protected amino acids as building blocks which are added to an amino acid or peptide residue attached to the solid support at the acyl (acid) end of the molecule. After the peptide bond has been formed, the protecting group is removed and the cycle repeated. When a peptide having the desired sequence has been synthesized, it is then removed from the support.

The second method, the inverse Merrifield method, employs reagents attached to solid supports in a series of columns. The amino acid or peptide residue is passed through these columns in a series to form the desired amino acid sequence.

These methods are well known in the art as discussed in U.S. Pat. Nos. 4,108,846, 3,839,396, 3,835,175, 4,508,657, 4,623,484, 4,575,541, 4,581,167, 4,394,519 as well as in *Advances in Enzymology*, 32, 221 (1969) and in PEPTIDES, VOL. 2, edited by Erhard Gross and Johannes Meienhoffer, Academic Press, New York, N.Y. pp. 3–255 (1980) and are incorporated herein by reference and is fully set forth herein.

During peptide synthesis, it may not be necessary to actually isolate the amino acid fluorides. The protected amino acid fluoride may be prepared in situ and then used in the coupling reaction with the carboxy protected amino acid or peptide. The fluoroformamidinium salts of the present invention permits the skilled artisan to accomplish these goals.

More specifically, in addition, to its use as a source of protected acid fluoride, the fluroformamidinium salts of the present invention can be used as coupling agents for peptide synthesis in which in situ formation of the intermediate acid fluoride precedes the coupling. This approach avoids the need to isolate, purify, and store the acid fluoride, yet allows one to take advantage of the great reactivity of this class of coupling compounds. Furthermore, under these circumstances, there is little, if any, racemization. For example,. the coupling reaction of Z-Phe-Val-OH with H-Ala-OMe carried out with the use of tetramethylfluoroformamidinium hexafluorophosphate, in the presence of proton sponge at −30° C. gives the expected tripeptide, with only about 1% racemization.

In addition to its use in the synthesis of protected amino acid fluorides and as a simple in situ coupling reagent, the fluoroformamidinium salts of the present invention, such as TFFH, can be used as a coupling agent for assembly of peptides by both solution and solid phase techniques. An example is the synthesis of leucine enkephalin H-Tyr-Gly-Gly-Phe-Leu-OH in 53% yield (88.5% purity) on an automated peptide synthesizer (Millipore 9050). Two other examples of solid phase syntheses involved synthesis of the nonamer prothrombin and the 20-mer alamethicin acid, H-Ala-Asn-Lys-Gly-Phe-Leu-Gly-Glu-Val-NH$_2$ and Ac-Aib-Pro-Aib-Ala-Aib-Ala-Gin-Aib-Val-Aib-Gly-Leu-Aib-Pro-Val-Aib-Glu-Gln-Phe-OH, respectively. The latter is unique in that it consists of many hindered amino acids, including α-aminoisobutyric acid (Aib), and could not previously be made by solid phase techniques except via FMOC amino acid fluorides.

The coupling reaction may also contain other additives normally utilized in peptide synthesis such as those utilized to prevent racemization. For example, besides the fluoroformamidinium salts, the following compounds may additionally be added to the coupling reaction:

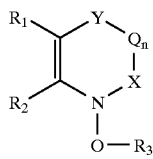

II and N-oxides thereof and salts thereof wherein

R$_1$ and R$_2$ taken together with the carbon atoms to which they are attached form a heteroaryl ring wherein said heteroaryl ring is an oxygen, sulfur or nitrogen containing heteroaromatic containing from 3 and up to a total of 13 ring carbon atoms, said heteroaryl may be unsubstituted or substituted with lower alkyl or an electron-donating group;

Y is O, NR$_4$, CR$_4$R$_5$;

R$_5$ is independently hydrogen or lower alkyl;

X is CR$_6$R$_7$ or NR$_6$;

R$_6$ or R$_7$ are independently hydrogen or lower alkyl; or R$_6$ and R$_7$ taken together form an oxo group or when n=0, R$_4$ and R$_6$ taken together may form a bond between the nitrogen or carbon atom of Y and the nitrogen or carbon atom of X;

Q is (CR$_8$R$_9$) or (NR$_8$);

when n is 1, R$_4$ and R$_8$ taken together may form a bond between the ring carbon or nitrogen atom of Q and the ring carbon or nitrogen atom of R$_8$;

n is 0, 1 or 2;

R$_3$ is hydrogen;

R$_8$ and R$_9$ are independently hydrogen or lower alkyl or R$_7$ and R$_8$ taken together with the carbon to 95 which they are attached form an aryl ring.

Examples include 1-hydroxy-7-aza-benzotriazole, 1-hydroxy-4-aza-benzotriazole, 1 hydroxy-4-methoxy-7-azabenzotriazole 4-N,N-dimethylamino-1-hydroxy-7-azabenzotriazole, 1-hydroxy-6-azabenzotriazole, 1-hydroxy-5-azabenzotriazole, 1-hydroxy-7-aza-1H-indazole, 1-hydroxyl-7-azabenzo-1H-imidazole, 1-hydroxy-1H-pyrrolo [2,3-b]pyridine, 1-hydroxy-4-t-butyl-7-azabenzotriazole, and the like. In addition, 1-hydroxy benzotriazole could also be utilized as the additive. These compounds as well as other compounds of Formula II are described in U.S. Pat. No. 5,580,981, the contents of which are incorporated by reference.

The amino acid fluorides of the present invention can exist in various stereoisomeric forms, viz., the D or L stereoisomers. Moreover, the amino acid fluorides may be present in mixture of the D and L forms such as in racemic mixtures. All of these forms are contemplated to be within the scope of the present invention. It is preferred that the stereoisomer of the amino acid fluorides of the present invention exist in the L form.

EXAMPLES

The invention will now be illustrated by examples. The examples are not intended to be limiting of the scope of the present invention. In conjunction with the general and detailed descriptions above, the examples provide further understanding of the present invention.

I Preparative Examples: Preparation of Cyanuric Fluoride

A 250 mL three necked round bottomed flask equipped with a thermometer, stirring bar, distilling apparatus and powder dropping funnel was charged with oven-dried sodium fluoride (53 g, 1.25 mole) and tetramethylene sulfone (sulfolane, TMS) (145 g, 115 mL, 1.20 mole, d=1.26). To the suspension was added cyanuric chloride (62 g. 0.33 mole) in small portions by use of the powder dropping funnel over a 10-min period. The reaction mixture was gradually heated to 250° C. by means of a heating mantle. The product distilled from the flask as formed and was collected in glass traps cooled in a Dry Ice-acetone bath. Collection of the distillate (29 mL) continued until distillation stopped (bp 72–78° C.). Redistillation gave 24 mL (86.19 g, 38.4% d=1.6 g/mL) of the fluoride as a clear colorless liquid, bp 72–73° C., lit bp 74° C.

II General Procedures for Preparation of N-(9-Fluorenyl-Methoxycarbonyl)Amino Acide Fluorides A solution (or suspension) of FMOC-amino acid (1 mmole) in dry CH$_2$Cl$_2$ (5 mL) was kept under nitrogen and treated with cyanuric fluoride (1.08 g, 8 mmol, 700 uL, d=1.6) and pyridine (81 uL, 1 mmole). A clear solution was obtained which was refluxed (or stirred at room temperature) for 45–120 min. Completion of reaction was checked by TLC. During the reaction a white precipitate separated. The mixture was extracted with ice-water (2×15 mL) which caused the precipitate to dissolve. The organic layer was dried over $MgSO_4$. Filtration and solvent removal gave a residue (solid or oil) which was crystallized from $CH_2Cl_2$/hexane or $Et_2O$/hexane to give the corresponding FMOC-N-protected amino acid fluoride as a white crystalline solid. The crude and recrystallized acid fluorides were analyzed by HPLC following the same technique described for the corresponding chlorides except that it was necessary to wait for 15–300 min following addition of the fluoride to dry methanol in order to allow time for complete conversion to the methyl ester. For example, a mixture initially analyzing for 93.45% FMOC-Gly-F (as methyl ester) came to complete conversion after 50 min with a measured content of 98.89% FMOC-Gly-OMe and 1.00% FMOC-Gly-OH. In case of FMOC-Val-F, initially analyzing for 82.70% FMOC-Val-F (as methyl ester) complete conversion occurred after 5 hours with a measured content of 98.19% FMOC-Val-OMe and 0.94% FMOC-Val-OH. Fischer esterification of the free acid in the methanolic HF solution did not occur. For example, a mixture initially containing 52.27% of FMOC-Gly-OH showed no significant change after 15 hours (52.19% acid) and the same results were observed in case of FMOC-Val-OH.

Example 1

N-(9-Fluorenylmethoxycarbonyl)glycine Fluoride:

The reaction was used in accordance with the procedure described above.

Reaction was completed after 2 hours of reflux, the fluoride being obtained in 80.5% yield as pale yellow needles, mp 140.1° C., (98.9% pure according to HPLC analysis); IR (KBr) 3337 (NH), 1843 (COF), 1680 (OCON) $cm^{-1}$; $^1$H NMR ($CDCl_3$) $\delta$4.1–4.3 (m, 3, $CHCH_2$), 4.5 (d, 2, $NCH_2CO$), 5.3 (bs, 1, NH), 7.15–7.8 (m, 8, aryl).

Anal. Calcd for $C_{17}H_{14}FNO_3$: C, 68.22; H, 4.71; N, 4.67. Found: C, 68.25, H, 4.63; N, 4.79.

Example 2

N-(9-Fluorenylmethoxycarbonyl)alanine Fluoride:

The reaction was run in accordance with the procedure described hereinabove.

Reaction was complete after 2 hours of reflux, the fluoride being obtained in 75.4% yield as a white solid, mp 111–2° C., (98.66% pure according to HPLC analysis); $[\alpha]D^{23}$+3.6° (c 0.5, EtOAc); IR (KBr) 3326 (NH), 1845 (COF), 1690 $cm^{-1}$; $^1$H NMR ($CDCl_3$) $\delta$1.6 (d, 3, $CH_3$), 4.2 (t, 1, $CHCH_2$), 4.5 (m, 3, $CH_2O$, NCHCO), 5.2 (d, 1, NH), 7.2–7.8 (m, 8, aryl).

Anal. Calcd for $C_{18}H_{16}FNO_3$: C, 69.00; H, 5.14; N, 4.47. Found: C, 69.16; H, 5.30; N, 4.30.

Example 3

N-(9-Fluorenylmethoxycarbonyl)valine Fluoride: The reaction was run in accordance with the procedure described hereinabove.

Reaction was complete after 2 hours of reflux, the fluoride being obtained in a yield of 70.2% as a white solid, mp 113–4° C., (98.62% pure according to HPLC analysis); $[\alpha]D^{24}$+10.7° (c 1, $CH_2Cl_2$); IR (KBr) 3312 (NH), 1843 (COF), 1688 (OCON) $cm^{-1}$; $^1$H NMR ($CDCl_3$) $\delta$1.0 (d, 6, $CH_3$), 2.3 (m, 1, $CHCH_2$), 4.2 (t, 1, $CHCH_3$), 4.5 (m, 3, $CH_2O$, NCHCO), 5.15 (d, 1, NH), 7.2–7.8 (m, 8, aryl).

Anal. Calcd for $C_{20}H_{20}FNO_3$: C, 70.36; H, 5.90; N, 4.10. Found: C, 70.27; H, 5.92; N, 4.19.

Example 4

N-(9-Fluorenylmethoxycarbonyl)leucine Fluoride:

The reaction was run in accordance with the procedure described above.

Reaction was complete after 1 hour of reflux, the fluoride being obtained in a yield of 75.2% as a white solid, mp 95.5–6.5° C., (98.58% pure according to HPLC analysis); $[\alpha]D^{23}$–5.8° (c 1, EtOAc); IR (KBr) 3336 (NH), 1938 (COF), 1699 (OCON) $cm^{-1}$; $^1$H NMR ($CDCl_3$) $\delta$1.00 (d, 6, $CH_3$), 1.6–1.8 (m, 3, $CH_2CH$), 4.2 (t, 1, $CHCH_2O$), 4.5 (m, 3, $CH_2O$, NCHCO), 5.1 (d, 1, NH), 7.2–7.8 (m, 8, aryl).

Anal. Calcd for $C_{21}H_{22}FNO_3$: C, 70.96; H, 6.23; H, 3.94. Found: C, 70.70; H, 6.48; N, 4.15.

Example 5

N-(9-Fluorenylmethoxycarbonyl)isoleucine Fluoride:

The reaction was run in accordance with the procedure described above.

Reaction was complete after 1.5 hours of reflux, the fluoride being obtained in a yield of 73.3% as a white solid, mp 115–6° C., (97.13%) pure according to HPLC analysis); $[\alpha]D^{23}$+15.6° (c 0.5, EtOAc); IR (KBr) 3304 (NH), 1840 (COF), 1996 (OCON) $cm^{-1}$; $^1$H NMR ($CDCl_3$) $\delta$1.00 (m, 6, $CH(Me)CH_2Me$), 1.1–1.6 (m, 2, $CHCH_2CH_3$), 2.00 (m, 1, CH), 4.2 (t, 1, $CHCH_2O$), 4.5 (m, 3, $CH_2O$, NCHCO), 5.2 (d, 1, NH), 7.2–7.8 (m, 8, aryl).

Analy. Calcd for $C_{21}H_{22}FNO_3$: C, 70.96; H, 6.23; N, 3.94. Found: C, 68.30; H, 6.06; N, 3.87.

Example 6

N-(9-Fluorenylmethoxycarbonyl)proline Fluoride:

The reaction was run in accordance with the procedure described above.

Reaction was complete after 12 hours of stirring at room temperature, the fluoride being obtained in a yield of 78.2% as a white solid mp, 88–9° C.; $[\alpha]D^{30}$–28.6° (c 0.5, EtOAc).

Anal. Calcd for $C_{20}H_{18}FNO_3$ C, 70.78; H, 5.34; N, 4.12. Found: C, 70.86; H, 5.43, N, 4.21.

Example 7

N-(9-Fluorenylmethoxycarbonyl)phenylalanine Fluoride:

The reaction was run in accordance with the procedure described above.

Reaction was complete after 1 hour of reflux, the fluoride being obtained in a yield of 63.9% as white crystals, mp 118–20° C., (99.3% pure according to HPLC analysis); $[\alpha]D^{24}$+35.5° (c 1, $CH_2Cl_2$); IR (KBr) 3318 (NH), 1843 (COF), 1700 (OCON) $cm^{-1}$; $^1$H NMR ($CDCl_3$) $\delta$3.2 (d, 2, $CH_2C_4H_5$), 4.2 (t, 1, $CHCH_2O$), 4.45 (m, 2, $CH_2O$), 4.85 (m, 1, NCHCO), 5.1 (d, 1, NH), 7.1–7.8 (m, 13 aryl).

Anal. Calcd for $C_{24}H_{20}FNO_3$: C, 74.03; H, 5.14; N, 3.59; F, 4.88. Found: C, 74.03; H, 5.13; N, 3.69; F, 4.68.

Example 8

N-(9-Fluorenylmethoxycarbonyl)tryptophan Fluoride:

The reaction was run in accordance with the procedure described above.

Reaction was complete after 1 hour of stirring at room temperature, the fluoride being obtained in a yield of 70.7% as a white solid, mp 125–8° C. (dec.) (98.2% pure according to HPLC analysis); $[\alpha]_D^{24}$ –5.2° (c 1, EtOAc); IR (KRr) 3390 and 3360 (NH), 1845 (COF), 1697 (OCON) cm$^{-1}$, $^1$H NMR (CDCl$_3$) δ3.4 (d, 2, CH$_2$CHCO), 4.2 (t, 1, CHCH$_2$O), 4.4 (d, 2, CHCH$_2$O), 4.9 (m, 1, NCHCO), 5.3 (d, 1, NH), 7.0–8.2 (m, 14, NH+aryl).

Anal. Calcd for C$_{33}$H$_{31}$FNO$_3$: C, 72.88; H, 4.94; N, 6.53. Found: C, 72.83, H, 5.01; N, 6.43.

Example 9

N-(9-Fluorenylmethoxycarbonyl)-O-(t-Butyl)serine Fluoride

The reaction was run in accordance with the procedure described above.

Reaction was completed after 1 hour of stirring at room temperature, the fluoride being obtained in a yield of 72.7% as white crystals, mp 89–91° C., (98.26% pure according to HPLC analysis); $[\alpha]_D^{26}$ +28.8° (, 5, EtOAc); IR (KBr) 3444 (NH), 1868 (COF), 1733 (OCON) cm$^{-1}$; $^1$H NMR (CDCl$_3$) δ1.2 (s, 9, CMe$_3$), 3.6 (q, 1, CHHOCMe), 3.9 (q, 1, CHHOCMe$_3$), 4.22 (t, 1, CHCH$_2$OCO), 4.45 (m, 2, CH$_2$OCO), 4.7 (m, 1, NCHCO), 5.65 (d, 1, NH), 7.25–7.8 (m, 8, aryl).

Anal. Calcd for C$_{22}$H$_{24}$FNO$_4$: C, 68.55; H, 6.27; N, 3.63. Found: C, 68.49; N, 6.32; N, 3.67.

Example 10

N-(9-Fluorenylmethoxycarbonyl)-O-(t-Butyl)threonine Fluoride:

The reaction was run in accordance with the procedure described hereinabove:

Reaction was complete after 1½ hours of stirring at room temperature, the fluoride being obtained in a yield of 72.6% as white crystals, mp 53.5° C., (98.03% pure according to HPLC analysis); $[\alpha]_D^{27}$ +12.3° (c 0.4 EtOAc); IR (KBr) 3320 (NH), 1857 (COF), 1726 (OCON) cm$^{-1}$; $^1$H NMR (CDCl$_3$) δ1.15 (s, 9, CMe$_3$), 1.3 (d, 3, CH$_3$), 4.3–4.5 (m, 5, CHCH$_2$OCO, NCH(CHO—)CO), 5.6 (d, 1, NH), 7.2–7.8 (m, 8, aryl).

Anal. Calcd for C$_{23}$H$_{22}$FNO$_4$: C, 69.15; H, 6.56; N, 3.50. Found: C, 69.11; H, 6.83; H, 4.00.

Example 11

N-(9-Fluorenylmethoxycarbonyl)-Nε-(t-Butyloxycarbonyl)-lysine Fluoride:

The reaction was run in accordance with the procedure described above.

Reaction was completed after 1 hour of stirring at room temperature, the fluoride being obtained in a yield of 65.9% as white crystals, mp128–30° C. (99.5% pure according to HPLC analysis); $[\alpha]_D^{23}$ –2.2° (c 0.5, CH$_2$Cl$_2$); IR (KBr) 2254 (NH), 1854 and 1836 (COF), 1693 (OCON) cm$^{-1}$; $^1$H (CDCl$_3$) 1.4 (s, 9, CMe$_3$), 1.5–2 (m, 6, CH$_2$—CH$_2$—CH$_2$), 3.15 (m, 1, CH$_2$NH), 4.2 (t, 1, CHCH$_2$O), 4.4–4.6 (m, 4, CH$_2$O, NCHCO, CH$_2$NH), 5.7 (d, 1, NH), 7.2–7.8 (m, 8, aryl).

Anal. Calcd For C$_{28}$H$_{31}$FN$_2$O$_5$: C, 66.36; H, 6.64; H, 5.95. Found: C, 66.16; H, 6.50; N, 5.92.

Example 12

N-(9-Fluorenylmethoxycarbonyl)aspartic Acid Fluoride-β-(t-Butyl) Ester:

The reaction was run in accordance with the procedure described above.

Reaction was completed after 30 minutes of stirring at room temperature, the fluoride being obtained in a yield of 67.8% as white crystals, mp 74–5° C., (97.97% pure according to HPLC analysis); $[\alpha]_D^{23}$ +4.00° (c 0.5, EtOAc); IR (KBr) 3320 (NH), 1856 (COF), 1725 (COO), 1695 (OCON) cm$^{-1}$, $^1$H NMR (CDCl$_3$) δ1.45 (s, 9, CMe$_3$), 2.9 (dq, 2, CH$_2$COO), 4.3 (t, 1, CHCH$_2$OCO), 4.5 (m, 2, CHCH$_2$O), 4.85 (m, 1, HCHCO), 5.85 (d, 1, NH), 7.2–7.8 (m, 8, aryl).

Anal. Calcd for C$_{23}$H$_{24}$FNO$_5$: C, 66.81; H, 5.85; N, 3.38. Found: C, 67.03; H, 5.95; N, 3.70.

The results of the above synthesis are summarized in the Table hereinbelow:

TABLE 1

Synthesis of FMOC-Amino Acid Fluorides

| Compound | Yield % | mp (° C.) | $[\alpha]_D^{t° C.}$ | |
|---|---|---|---|---|
| FMOC—Gly—F | 80.5 | 140–1 | | |
| FMOC—Ala—F | 75.4 | 111–2 | +3.6° | (c 0.5, EtOAc, 23) |
| FMOC—Val—F | 70.2 | 113–4 | +10.7° | (c 1, CH$_2$Cl$_2$, 24) |
| FMOC—Leu—F | 75.2 | 95–6 | –5.8° | (c 1, EtOAc, 23) |
| FMOC—Ile—F | 73.3 | 115–6 | +15.6° | (c 0.5, EtOAc, 23) |
| FMOC—Phe—F | 63.9 | 118–20 | +35.5° | (c 1, CH$_2$Cl$_2$, 24) |
| FMOC—Trp—F | 70.7 | 125–8 | –5.2° | (c 1, EtOAc, 24) |
| FMOC—Ser(tBu)—F | 72.7 | 89–91 | +28.8° | (c 0.5, EtOAc, 26) |
| FMOC—Thr(tBu)—F | 72.6 | 53–5 | +12.3° | (c 0.4, EtOAc, 27) |
| FMOC—Lys(BOC)—F | 65.9 | 128–30 | –2.2° | (c .5, CH$_2$Cl$_2$, 24) |
| FMOC—Asp(OtBu)—F | 67.8 | 74–5 | +4.0° | (c 0.5, EtOAc, 23) |

These results indicate that cyanuric fluoride is suitable not only for the preparation of simple FMOC-amino acid fluorides but also for those containing t-BOC, t-Bu or CBZ-groups on the side chain. The amino acid fluorides described hereinabove were obtained in crystalline form.

The use of amino acid fluorides of the present invention being used as peptide coupling agents is illustrated hereinbelow.

In the following example, the FMOC amino acids were utilized:

Example 13

Use of FMOC-AA-F in Peptide Synthesis

I General Method for Executing Rapid FMOC/4-AMP or FMOC/TAEA Peptide Synthesis. Five millimeters of a 0.1M solution of the C-terminal starting amino acid ester, 5 mL of CHCl$_3$ containing 0.75 mmol of the appropriate

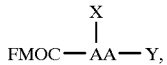

(wherein Y is halo, i.e., chloro or fluoro) and 5 mL of 5% Na$_2$CO$_3$ solution were combined and the two phase mixture stirred vigorously for 10 minutes. The organic phase was separated and treated with 5 mL of 4-AMP or TAEA. After 30 minutes 40 mL of CHCl$_3$ was added and the organic phase washed with five 25-mL portions of 10% phosphate buffer of pH 5.5. Alternatively two 25-mL portions of saturated NaCl solution was used to remove excess 4-AMP or TAEA prior to extractions with the phosphate buffer. The organic phase was concentrated in vacuo to a volume of 5 mL on a rotary evaporator and the resulting CHCl$_3$ solution used analogously for treatment with the next FMOC amino acid halide.

II Preparation of FMOC-Val-Asp(CMe$_3$)-Val-Leu-Leu-Ser(CMe)$_3$-Tyr(CMe$_3$)-OCMe$_3$. The general procedure described above was followed beginning with 330 mg (1 mmol) of H-Tyr-(CMe$_3$)-OCMe$_3$ HCl, 462 mg (1.2 mmol) of FMOC-Ser-(CMe$_3$)-F, 10 mL of methylene dichloride and 10 mL of 5% sodium carbonate solution. The mixture was stirred for 15 minutes, the organic layer separated and treated with 7.5 mL of TAEA for 30 minutes. The solution was washed with three 10-mL portions of said sodium chloride solution and three 15-mL portions of phosphate buffer (pH 5.5). The organic layer was then treated in the same way in sequence with the remaining FMOC amino acid halides (FMOC-Leu-Cl twice, FMOC-Val-Cl, FMOC-Asp(CMe$_3$)-F and FMOC-Val-Cl a second time). Evaporation of the organic layer was followed by column chromatography to give the protected heptapeptide, mp 249–251° C., in 50–60% yield MSFAB: 1255 (M+1); calculated 1253.8 (M).

Example 14

Coupling of FMOC-Phe-F with H-Leu-OMe. Five millimeters of a 0.1M solution of H-Leu-OMe in CHCl$_3$ was treated with 5 mL of CHCl$_3$ containing 0.6 mmol of FMOC-Phe-F (mp 118–120°) and 5 mL of 5% Na$_2$CO$_3$ solution. The two-phase mixture was stirred vigorously for 10 minutes, the layers separated and the organic layer dried over MgSO$_4$ and evaporated with a rotary evaporator. Without purification the crude residue (90%) was examined by HPLC analysis which showed no evidence for the DL-diastereomer (0.1%). The two diasteromers are readily separated with a mobile phase consisting of 1% isopropyl alcohol in hexane (retention times: LL, 13.26 minutes; DL-17.13 minutes at flow rate 1.5 mL/minutes) using a Waters Radial Pak normal silica gel column 10 u, Z-module fitting.

Example 15

CBZ-alanine Fluoride

CBZ-Ala (1 mmole) in dry CH$_2$Cl$_2$ is kept under nitrogen and treated with cyanuric fluoride (8 mmol) and pyridine (1 mmole) to form the corresponding CBZ-Ala-F.

Example 16

N-formyl-O-(t-butyl) serine Fluoride

N-formyl serine (1 mmole) in dry CH$_2$Cl$_2$ under nitrogen is treated with cyanuric fluoride (8 mmol) and pyridine (1 mmol) to form the above-identified product.

Example 17

2-(t-butylsulfonyl)-2-propenyl-oxycarbonyl-1-phenylalanine Fluoride

A. t-Butyl Allyl Sulfide. To a solution of 350 mL of anhydrous ethanol maintained under nitrogen was slowly added 22.99 g (1 mol) of sodium spheres. The sodium dissolved within 90 minutes, and to the resulting sodium ethoxide solution was added 90.19 g (1 mol) of t-butyl mercaptan with mechanical stirring. Allyl bromide (120.98 g; 1 mol) was then added dropwise to the mechanically stirred sodium t-butyl thiolate solution. After the addition was complete, the mixture was refluxed for 10 minutes, the solution allowed to cool, the precipitated sodium bromide filtered, and the ethanol removed by distillation at atmospheric pressure. The residue was diluted with 200 mL of water, and the layers separated. The aqueous layer was extracted with five 40-mL portions of ether. The combined organic layers were extracted with 150 mL of water, the organic layer dried over MgSO$_4$, filtered, and the solvent removed in vacuo from a water bath at 45° C. to give a yellow liquid. Distillation through a 0.8×15-cm fractionating column gave 56.16 g (45%) of the sulfide as a colorless liquid, bp 139–141° C.

B. 1,3-Dibromo-2-(t-butylsulfonyl) Propane. To a stirred solution of 17.37 g (0.13 mol) of t-butyl allyl sulfide in 133 mL of CCl$_4$ at −24° C. (CCl$_4$/dry ice) was added dropwise a solution of 21.33 g (0.13 mol) of Br$_2$ in 67 mL of CCl$_4$. A yellow solid precipitated during the addition. The mixture was warmed to room temperature and stirred for 10 minutes following complete solution of the yellow solid. The resulting solution was poured into a mixture of 55.50 g (0.27 mol) of 85% m-chloroperbenzoic acid in 490 mL of CH$_2$Cl$_2$ kept at −24° C., and the mixture stirred for 30 minutes at this temperature. The cooling bath was then removed and the mixture stirred at room temperature overnight. The precipitated m-chlorobenzoic acid was filtered and the filtrate washed with three 200-mL portions of saturated NaHCO$_3$, followed by 200 mL of water. The organic layer was dried over MgSO$_4$, filtered, and the solvent removed in vacuo from a water bath at 45° C. The crude product was recrystallized from 20% EtOAc/Skelly B to give 32.02 g (75%) of the dibromide, mp 139–140° C.

C. 2-(t-Butylsulfonyl)-2-propenyl Bromide. A mixture of 16.78 g (0.052 mol) of 1,3-dibromo-2-(t-butylsulfonyl) propane and 14 mL (0.12 mol) of 2,6-lutidine in 55 mL of CH$_2$Cl$_2$ was refluxed for 75 minutes. The solution was allowed to cool to room temperature and extracted with three 80-mL portions of 5% HCl followed by 80 mL of water. The organic layer was dried over MgSO$_4$, filtered, and the solvent removed in vacuo from a water bath at 45° C. to give 11.46 g (91%) of the allyl bromide as a white solid, mp 40.5–42.0° C., which was used without further purification.

D. 2-(t-Butylsulfonyl)-2-propenyl Alcohol. A mixture of 8.55 g (35.3 mmol) of 2- (t-butylsulfonyl)-2-propenyl bromide and 5.31 g (78.1 mmol) of sodium formate in 150 ml of methanol was refluxed overnight. The solution was allowed to cool and concentrated to 50 mL with the aid of a water aspirator, resulting in the precipitation of excess sodium formate. The residue was diluted with 150 mL of water and extracted with five 50-mL portions of CH$_2$Cl$_2$. The organic layer was dried over MgSO$_4$, filtered, and the solvent removed in vacuo from a water bath at 45° C. The crude product was recrystallized from 15% EtOAc/Skelly F to give 4.30 g (68%) of the alcohol as a colorless solid, mp 53.5–54.5° C.

E. 2-(t-Butylsulfonyl)-2-propenyl Chloroformate. To a solution of 6.67 g (37.4 mmol) of 2-(t-butylsulfonyl)-2-propenyl alcohol in 27 mL of dry THF at 0° C. was added in one portion 27 mL of phosgene. The solution was stirred for 1 hour at 0° C. and allowed to stand at room temperature overnight. Excess phosgene and solvent were removed under reduced pressure. The crude product was recrystallized from 25% ether/Skelly B to give 8.23 g (91%) of the chloroformate as a colorless solid, mp 56.5–57.7.

F. 2-(t-Butylsulfonyl)-2-propenyloxycarbonyl-L-phenylalanine. A solution of 4.57 g (19.0 mmol) of 2- (t-butyl-sulfonyl)-2-propenyl chloroformate and 5.64 g (18.6 mmol) of t-butyl L-phenylalaninate hydrophosphite in 90 mL of CH$_2$Cl$_2$ was stirred in the presence of 165 mL of 5%

NaHCO$_3$ at room temperature for 2 hours. The aqueous phase was separated, and the organic phase washed with three 75-mL portions of 5% HCl. The organic phase was dried over MgSO$_4$, filtered, and the solvent removed in vacuo from a water bath at 45° C. The resulting oil was dissolved in 36 mL of 50% CH$_2$Cl$_2$/trifluoro-acetic acid, and the solution stirred at room temperature for two hours. Excess trifluoracetic acid and solvent were removed in vacuo from a water bath at 150° C. The resulting oil was crystallized from ether/Skelly F to give approximately 6.25 g (91%) of the colorless acid, mp 88.0–89.5° C.

G. 2-(t-butylsulfonyl)-2-propenyloxycarbonyl-L-phenyl-alanine fluoride. The product formed hereinabove in Example 17F (1 mmol) is placed in dry CH$_2$Cl$_2$ under nitrogen and treated with cyanuric fluoride (8 mmol) and pyridine (1 mmol) to form the above-identified product.

Example 18

BOC-Phe-F.

BOC-Phe (1 mmole) in dry CH$_2$Cl$_2$ under nitrogen is treated with cyanuric fluoride (8 mmol) and pyridine (1 mmole) to form the above-identified product.

Example 19

Coupling of Bspoc-Phe-F with H-Leu-OMe

Five milliliters of 0.1M solution of H-Leu-OMe in CHCl$_3$ was treated with 5 ml of CHCl$_3$ containing 0.6 mmol of Bspoc-phe-F and 5 ml of 5% Na$_2$CO$_3$ solution. The two phase mixture is stirred vigorously for 10 minutes, the layers separated and the organic layer dried over MgSO$_4$ and evaporated to afford the coupled dipeptide.

Bspoc-Phe-Leu-OMe

Example 20

BIMOC-Phe-F

A. 1-Bromo-2-bromomethylnaphthalene. To a solution of 103 g of 1-bromo-2-methylnaphthalene (bp 98–120°/0.5 mm, prepared in 90% yield by the method of Adams and Binder in JACS, 63, 2771(1941) and 82 g or N-bromosuccinimide in 1030 mL of CCl$_4$ was added 0.54 g of dibenzoyl peroxide. The reaction mixture was refluxed with stirring for 3 h. After another 0.54 g of dibenzoyl peroxide was added, the mixture was refluxed for 3 hours. The solution was allowed to stand at room temperature overnight, and the resulting suspension was brought to the boiling point and filtered while hot. Concentration of the filtrate gave 139 g (99.4%) of the bromide as a light yellow solid, mp 104–107° C., which was recrystallized from CCl$_4$ to give 128 g (91.6%) of pure 1-bromo-2-bromomethylnaphthalene as colorless crystals, mp 106.5–107.5° C.

B. Diethyl 2-(1-Bromo-2-naphthylmethyl)malonate. To a solution of NaOEt prepared from 9.66 g of sodium and 210 mL of dry EtOH was added 63.76 mL of diethyl malonate and the reaction mixture refluxed for 2 h. To the resulting yellow solution was added in small portions 126 g of 1-bromo-2-bromomethylnaphthalene and the reaction mixture refluxed for 16 h. Distillation of ethanol from an oil bath (100–110° C.) through a simple Claisen head gave a yellow suspension, to which was added 350 mL of CH$_2$Cl$_2$ and 350 mL of H$_2$O. The aqueous layer was extracted twice with 120-mL portions of CH$_2$Cl$_2$, and the combined organic layer was washed three times with 100-mL portion of H$_2$O, dried (MgSO$_4$) and evaporated to give 152 g (95.6%) of the ester as a yellow solid, mp 60–65° C. Recrystallization from acetic acid gave 137 g (86.2%) of the pure diester as a colorless solid, mp 77–79° C.

C. β-(1-Bromo-2-naphthyl)propionic Acid. To a solution of 160 g of the product formed in B hereinabove in 239 mL of methanol was added 538 mL of 5N NaOH solution. The mixture was refluxed for 135 min, and cooled by means of an ice bath to 0° C. To the reaction mixture was added 320 mL of ice water, and the resulting precipitate was collected by filtration and washed several times with small portions of ice water. To the ice-cold, stirred filtrate was added dropwise 5N HCl solution until the solution was weakly acidic. The precipitate was filtered and washed several times with small portions of water. Drying gave 86 g (63.1%) of crude diacid as a light yellow solid, mp 154–157° C. Recrystallization from water gave 80 g (58.7%) of pure diacid as colorless crystals, mp 157–159° C. A suspension of 47.5 g of the crude malonic acid in 968 mL of 6N HCl solution was refluxed for 16 h. The mixture was cooled by means of an ice bath to 0° C., treated with 650 mL of CH$_2$Cl$_2$, and stirred for 15 min. The aqueous layer was extracted twice with 100-mL portions of water, dried (MgSO$_4$), and evaporated to give 30.3 g (74%) of yellow solid, mp 116–119° C., which was recrystallized from alcohol to give 28 g (68%) of the acid as colorless crystals, mp 123–124° C.

D. β-(1-Bromo-2-naphthyl)propionyl chloride. To a solution of 40.16 g of the product formed in C hereinabove in 802 mL of CH$_2$Cl$_2$ was added 19.3 mL of thionyl chloride. The mixture was refluxed for 4 h, cooled to room temperature, and the solvent evaporated from a water bath (40–50° C.) with a rotary evaporator (10 mm) to give a red-brown residue. In order to remove traces of thionyl chloride, small portions of CH$_2$Cl$_2$ were added and the solution reevaporated three times. Eventually the crude acid chloride was obtained as a red-brown oil. The crude product was used immediately for the next step without further purification.

E. 4-Bromobenz[f]indan-1-one. To an ice cold, stirred solution of the above crude β-(1-bromo-2-naphthyl) propionyl chloride in 802 mL of dry CH$_2$Cl$_2$ was added 26.11 g of anhydrous AlCl$_3$ carefully. The reaction mixture was refluxed for 2 h, cooled to room temperature and treated carefully while stirring with 900 mL of ice-water followed by 75 mL of conc. HCl. The brown precipitate was filtered and washed five times with small portions of CH$_2$Cl$_2$. The aqueous layer was separated and extracted twice with 100-mL portions of CH$_2$Cl$_2$. The combined CH$_2$Cl$_2$ extracts were washed three times with small portions of H$_2$O, dried (MgSO$_4$) and evaporated from a water bath (50–60° C.) with a rotary evaporator (7 mm) to give 30.1 g (80.1%) of the crude ketone as a yellow solid, mp 146–149° C., which could be recrystallized from acetic acid to give 28.5 g (76%) of the pure ketone as colorless crystals, mp 149–151° C.

F. Benz[f]indan-1-ol. To an ice-cold solution of 22 g of the product formed in E hereinabove in 150 mL of dry THF was added carefully in small portions 16.1 g of LiAlH$_4$. Subsequently, another 270 mL of dry THF was added to the suspension and the mixture was refluxed for 8 days. The reaction mixture was cooled to 0° C. by means of an ice-bath and treated dropwise with 50 mL of ice-water followed by 1080 mL of 10% H$_2$SO$_4$ solution. The mixture was extracted three times with 100-mL portions of ether and the combined ether extracts washed three times with 150-mL portions of H$_2$O, dried (MgSO$_4$), and evaporated from a water bath (60–70° C.) with a rotary evaporator (10 mm) to give 9.2 g (59.3%) of the crude alcohol as a light yellow solid, mp 135–139° C. Recrystallization from benzene (45 mL) gave 8.6 g (55.4%) of pure alcohol as colorless crystals, mp 139–141° C.

G. Benz[f]indene. A solution of 8.6 g of benz[f]indan-1-ol in 250 mL of 10% H$_2$SO$_4$ was refluxed for 24 h. After cooling to room temperature the reaction mixture was extracted with three 150-mL portions of a mixture of benzene and hexane (1:2). The extracts were washed three times with 100-mL portions of water, dried (MgSO$_4$), and evaporated to give 7.6 g (98%) of a colorless solid, mp 160–163° C. Recrystallization from 340 mL of 95% ethanol gave 6.6 g (85%) of the hydrocarbon as colorless crystals: mp 163–164° C.

H. Benz[f]indene-1-methanol. A 1.0M solution of n-butyllithium (44 mL, 44 mmoles) was added dropwise under a nitrogen atmosphere to a stirred solution of 5 g (30.12 mmoles) of benz[f]indene in 140 mL of anhydrous ether and 20 mL of anhydrous THF cooled by means of a Dry Ice-acetone bath to −70° C. The temperature of the reaction mixture was not allowed to exceed −50° C. Benzindenyl lithium soon started to precipitate as small red crystals. After completion of the addition (about 2 hours), the reaction mixture was stirred at −70° C. for another 45 minutes before introduction of formaldehyde. Paraformaldehyde, 13.5 g. dried overnight in vacuum over phosphorus pentoxide, was stirred and heated in a dry flask placed in an oil bath at 175–195° C. The formaldehyde gas was led through a 7-mm glass tube into the benz[f]indenyl lithium solution (held below −50° C.) by a stream of dry nitrogen. The temperature was not allowed to exceed −50° C. After completion of the addition, 280 mL of 10% HCl solution was slowly poured into the stirred reaction mixture. The mixture was stirred for 15 minutes at room temperature. After the ether layer was separated, the aqueous solution was extracted twice with 50-mL portions of ether and the combined ether solution was washed with small portions of water until neutral. The ether solution was dried (MgSO$_4$) and evaporated to give a light brown oil (6 g). Storage in the freezer gave a soft yellow solid which was purified by chromatography (100 g of silica gel, 1:1 ethyl acetate/hexane) to give 3.5 g (59%) of the alcohol as a yellow solid. The NMR showed the solid to be a mixture of benz[f]indene-1-methanol (95%) and benz[f]indene-3-methanol. Several recrystallizations from ligroin (bp 88–89° C.) gave 3.0 g (50.6%) of pure, colorless benz[f]indene-1-methanol: mp 115–116° C.

M. The BIMOC-Phe (1 mmole) formed in L hereinabove in dry CH$_2$Cl is kept under nitrogen and treated with Cyanuric fluoride (8 mmol) and pyridine (1 mmol) to form the corresponding BIMOC-Phe-F.

Example 21

Benz[e]indene-3-methyloxycarbonyl-phenylalanine acid fluoride

A. Benz[e]-indene-3-methanol

1-Keto-4,5-benzindane-3-carboxylic acid, [which was prepared in accordance with the procedure described by T. N. Poltabiraman and W. B. Lawson in *J.Biol. Chem*, 247, 302a (1972) the contents of which are incorporated herein by reference] is reduced by sodium borohydride to form the corresponding 3-carboxylic acid -1-ol. Dehydration with sulfuric acid give the corresponding unsaturated acid. The unsaturated acid was then reduced by LiAlH$_4$ to form the 3-methanol derivative:

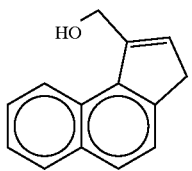

B. N-[Benz[e]indene-3-methyloxycarbony] phenylalanine. This product is prepared from the product of A hereinabove by following the procedure described in Ex. 20 I-L hereinabove C. N-[Benz[e] indene 1-methoxycarbonyl] phenylalanine acid fluoride The product B formed hereinabove (1 mmol) in dry Ch$_2$Cl$_2$ is kept under nitrogen and treated with cyanuric fluoride (8 mmol) and pyridine (1 mmol) to form the above product.

Example 22

Benz[e]indene-1-methyloxy carbonylphenylalanine acid fluoride

A. Benz[e]-indene-1-methanol

3-Keto-4,5-benzindan-1-carboxylic acid, which was prepared in accordance with the procedure described by T. N. Paltabiraman and W. B. Lawson, in *J. Biol. Chem.* 242, 3029(1941) is reduced to the corresponding 1-carboxylic acid-3-ol- by NaBH$_4$. Dehydration with H$_2$SO$_4$ gave the unsaturated acid which was then reduced to benz(e)-indene-1-methanol by means of LiAlH$_4$.

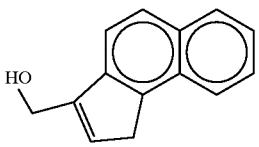

B. N-(Benz[e]indene-1-methyloxycarbonyl) phenylalanine

This product is prepared from the product of A hereinabove by following the procedure described in Ex. 20 I-L hereinabove C. N-[Benz(e) indene-1-methoxyoxy carbonyl] phenylalanine acid fluoride.

The product B formed hereinabove (1 mmol) in dry CH$_2$Cl$_2$ is kept under nitrogen and treated with cyanuric fluoride (8 mmol) and pyridine (1 mmol) to form the above product.

Example 23

N-[Benz(e) indene 1-methoxy carbonyl]phenylalanine acid fluoride and N[Benz(e) indene 3-methoxy carbonyl] phenylalanine acid fluoride 2(β)-naphthylpropionic acid is treated with thionyl chloride and cyclized in the presence of aluminum chloride to form the corresponding ketone. Reduction of the ketone with sodium borohydride, followed by dehydration with sulfuric acid gives the benz[e] indene. Formylation with ethyl formate and sodium hydride followed by treatment with sodium borohydride gave a mixture of the Benz[e] indene-3-methanol and Benz[e]-indene-1-methanol. The two alcohols are separated by chromatography.

Following the procedures in Examples 22 B-C and 23 B-C, the above-identified products are prepared.

It is to be noted from the preparations hereinabove that Benz[e]indene 1-methoxycarbonyl and the benz[e] indene-3-methoxy carbonyl can be used to protect the Nα-amino group of an amino acid.

These groups are formed from the corresponding alcohol, as described in Ex. 21–23. The alcohols are then used as starting materials to form the corresponding chloroformates and azidoformates, as described in Ex. 20. The azidoformate can then be reacted with an amino acid in accordance with the procedure described in Ex. 20-L to form the corresponding Nα-protected amino acid. This then is treated with cyanuric fluoride to form the corresponding amino acid fluoride.

Example 24

TFFH (a) Synthesis of Tetramethylchloroformamidinum hexafluorophosphate (TCFH). A 20% solution of phosgene in toluene (100 mL) was added dropwise and under dry conditions to a solution of tetramethylurea (11.6 g) in toluene. After approximately 15 min, when the carbon dioxide evolution had stopped, anhydrous ether (350 ml) was added under vigorous stirring. The precipitated salt was filtered and washed with anhydrous ether (3×50 mL). The highly hygroscopic material was immediately dissolved in dichloromethane (500 mL) and to this solution a saturated solution of potassium hexafluorophosphate (30 g/30 mL) was added under continuous stirring for 10–15 min. The organic phase was washed with water (40 mL), dried ($MgSO_4$), and the solvent removed under reduced pressure to give 24.8 g (88.8%) of the salt as a white solid, mp 90–92° C.; $^1$H NMR ($CDCl_3$, DMSO-$d_6$): δ 3.3 (s, $CH_3$). The same compound was prepared by using oxalyl chloride instead of phosgene but in this case the reaction mixture was refluxed for 2 hrs. A yield of 85.6% was obtained.

(b) Synthesis of Tetramethylfluoroformamidinium Hexafluorophosphate (TFFH). To a solution of TCFH (5.6 g) dissolved in dry acetonitrile (30 mL) there was added 20 mmol of KF (1.16 g, dried in the oven for one night) portionwise and the reaction mixture was stirred at room temperature for 2–3 hrs. The insoluble solid (KCl) was filtered and the filtrate was evaporated with a rotary evaporator and the residue recrystallized from acetonitrile-ether to give 4.3 g (92.3%) of the salt as white crystals, mp 111–112° C.; $^1$H NMR ($CDCl_3$, DMSO-$d_6$); δ 3.17–3.18 (d, $CH_3$). Anal. Calcd for $C_5H_{12}F_7N_2P$ (mol. wt. 264); C, 22.72; H, 4.55; N, 10.61. Found: C, 22.73; H, 4.50; N, 10.63.

Example 25

Large Scale Synthesis of TFFH

The method described above was used except that 120 mL of tetramethylurea, 200 mL of phosgene and 1000 mL of toluene were used with 2-h stirring for the first step. After filtering and washing with anhydrous ether the white salt was dissolved in 1500 mL of $CH_2Cl_2$ and the solution stirred vigorously during the addition of a saturated solution of 180 g of $KPF_6$ in 200 mL of water (10–15 min). Then 100 mL of water was added, the mixture shaken well in a separatory funnel and the $CH_2Cl_2$ layer collected and dried. Removal of solvent gave 224.6 g (80.1%) of the chloro salt. To 140.3 g (0.5 mmol) of the chloro salt dissolved in 300 mL of $CH_3CN$ was added with vigorous stirring 29 g (0.5 mmol) of KF. $^1$H-NMR was used to follow the reaction as the chloro derivative (δ 3.5 s) was converted to the fluoro compound (δ 3.3, 3.29 d). After 2–3 h reaction was complete. Filtration of KCl, evaporation and recrystallization from $CH_3CN/Et_2O$ gave 108 g (81.8%) of fluoro salt, mp 108–109° C.

Example 26

Trimethylphenylfluoroformamidinium Hexafluorophosphate (TPFFH).

N,N-Dimethylcarbamyl chloride (21.4 g, 0.2 mol) was added to a solution of 43.3 (0.4 mol) of N-methylaniline in 200 mL of $CH_2Cl_2$ and the solution stirred at room temperature for 5 h. The reaction was followed by TLC (EtOAc/hexane) and after 8 h, 200 mL of $CH_2Cl_2$ was added followed by 150 mL of 20% hydrochloric acid. The mixture was stirred for 1 h, the $CH_2Cl_2$ layer was collected, washed twice with water (200 mL), dried and evaporated to give a colored liquid which was distilled twice to give 21.4 g (60.1%) of the urea, bp 130–140° C. (1.5–2 mm), $^1$H NMR ($CDCl_3$) δ 2.75 (s, 6, $CH_3$), 3.2 (s, 3, $CH_3$), 7–7.6 (m, 5 aryl). To 32.3 g of the urea obtained as described in 100 mL of toluene cooled to −30 to −10° C. there was added 300 mL of a 20% solution of phosgene in toluene. The mixture was stirred at this temperature for 1 h and the temperature then allowed to come to room temperature after which the mixture was stirred overnight, filtered, the solid washed with ether and dissolved in 500 mL of $CH_2Cl_2$. The solution was stirred vigorously while 90 g of $KPF_6$ in 120 mL of water was added over 15 min. Water (100 mL) was added and the mixture shaken well in a separatory funnel. The organic layer was collected, dried and evaporated to give 51.9 g (84.0%) of the chloro salt (TPCFH) as a white solid, mp 120–125° C. (changing to a red-colored material at 180° C.), $^1$H-NMR ($CD_3COCD_3$) δ 3.4 (s, 6, $CH_3$), 3.8 (s, 3, $CH_3$), 7.6 (s, 5, aryl). To 30 g (87.6 mmol) of TPCFH dissolved in 60 mL of dry $CH_3CN$ was added with vigorous stirring 5.2 g of KF (90 mmol). The mixture was stirred at room temperature for 2–3 h, the reaction being followed by $^1$H-NMR spectroscopy. The mixture was filtered and evaporation of the filtrate gave 25.5 g (89.3%) of the fluoro salt after recrystallization from $CH_3CN/Et_2O$ as a white solid, mp 83–84° C., $^1$H-NMR ($CD_3COCD_3$) δ 3–3.5 (m, 6, $CH_3$), 3.8 (d, 3, $CH_3$), 7.6 (s, 5, aryl).

Example 27

Bis(tetramethylene)fluoroformamidinium hexafluorophosphate (BTFFH).

To 0.01 mol of the chloro salt dissolved in 100 mL of dry acetonitrile was added in one portion at rt, 0.015 mol of KF (dried in an oven for 24 h). The reaction mixture was stirred overnight at rt, filtered from KCl and washed with acetonitrile. The solvent was removed in vacuo and the residual oily compound was dissolved in acetonitrile and precipitated by ether. The solid was filtered and washed with ether three times (100 mL each). The crude sample is pure enough for further use. In order to obtain a sample for elemental analysis, it was recrystallized from $CH_2Cl_2$/ether which gave white crystals, mp 153–155° C.; yield 85.2%; $^1$H NMR ($CD_3CN$) δ 2.03 (m, 4H), 3.84 (m, 4H).

Anal. Calcd for $C_9H_{16}N_2PF_7$: C, 34.17; N, 5.06; N, 5.06; N, 8.86. Found: C, 34.29, H, 5.09; N, 8.76.

Example 28

1,3-Dimethyl-2-fluoroimidazolium Hexafluorophosphate (DFIH).

This compound was prepared from the corresponding chloro salt and KF by the same method described above except that a reaction time of 3h was used. The reaction can be followed by $^1$H NMR, by watching the methylene singlet convert to a doublet. Recrystallization from $CH_2Cl_2$/ether gave in 87.2% yield, white crystals, mp 168–169° C.; $^1$H NMR (CD$_3$CN) δ 2.9 (s, 6H, CH$_3$), 3.88 (d, 4H, CH$_2$); IR (KBr) 1716, 1633 (C=N$^+$) cm$^{-1}$.

Anal. Calcd for C$_5$H$_{10}$N$_2$PF$_7$: C, 22.9; H, 3.82; N, 10.69. Found: C, 22.1; H, 3.69; N, 10.39. The NMR spectrum showed about 10% of the urea and if the analysis is calculated on this basis the results agree with theory: C, 21.9; H, 3.60; N, 10.22.

Example 29

Tris(1-Pyrrolidino)fluorophosphonium hexaflurophosphate(PyFLOP)

To 10 mmol of Tris(1-pyrrolidino)-bromophosphoium hexaflurophosphate (PyBrOP) dissolved in 30 mL of dry CH$_3$CN was added 12 mmol of KF in one portion, and the mixture stirred at rt overnight and filtered from the KBr. A test with AgNO$_3$ gave a heavy yellow precipitate. Acetonitrile was removed in vacuo and the residue was recrystallized from CH$_2$Cl$_2$/ether to give white crystals, mp 116–118° C.; yield 7.9%; $^1$H NMR (CD$_3$CN) δ 1.8–2.1 (m, 12 H, CH$_2$), 3.1–3.5 (M, 12H, CH$_2$).

Anal. Calcd for C$_{12}$H$_{24}$N$_3$P$_2$F$_7$: C, 35.56; H, 5.931 N; 10.37. Found C, 35.28; H, 5.91; N, 10.16.

Example 30

Synthesis of Acid Fluorides Using Fluoroformamidinium Salts. General Method.

To 1 mmol of protected amino acid dissolved in 5 mL of CH$_2$Cl$_2$ (dry), 1 mmol of DIEA (diisopropyl ethylamine) was added, followed by addition of 1.5 mmol of the fluoro formamidinium salt in 5–10 mL of dry CH$_2$Cl$_2$ under N$_2$. The reaction mixture was stirred at rt for about 3 h. IR examination showed absorption at 1842 cm$^{-1}$ after 3–5 min indicative of the COF group, but TLC analysis showed starting material even after 1 h. After complete reaction CH$_2$Cl$_2$ can be added and the reaction mixture washed three times with crushed ice-water (10 mL), and the solution dried. The solvent was removed and the residue recrystallized from CH$_2$Cl$_2$/hexane.

The following examples were prepared using the above methodology.

| Fluoro salt | Acid Fluorides | mp | Yield (%) |
|---|---|---|---|
| DFIH | Z—Phe—F | 81–83° C. | 55.6 |
|  | Z—Ala—F | 32–6° C. (from hexane) | 54.8 |
|  | Fmoc-Phe—F | 111–113° C. | 60.2 |
| BTFFH | Z—Phg—F | 72–75° C. | 60.7 |
|  | ⊖Z—Phe—F | 110–113° C. | 63.2 |
|  | Fmoc-Tyr(tBu)—F | 96–98° C. | 63.4 |
| TFFH | Z—Phg—F | 73–75° C. | 68.9 |

Example 31

Preparation of Acid Fluorides by Use of TFFH. General Method: One mmole of a protected amino acid and 1 mmole of pyridine were dissolved in 10 mL of dry methylene chloride and 1.5 mmole of TFFH was added under nitrogen. The reaction mixture was stirred at room temperature for 3 hrs after which ice-water was added and the organic layer separated and washed with additional ice-cold water (2×10 mL), dried (MgSO$_4$), and the solvent removed to give an oil which was recrystallized from methylene chloride-hexane.

Using this procedure, the following amino acid fluorides were prepared:

(a) FMOC—Val—F: Mp 109-110° C., 67%

IR, 1842 (C(=O)—F) cm$^{-1}$; $[\alpha]^{24}$ = +10.1, c = 1, CH$_2$Cl$_2$.

(b) FMOC—Phe—F: Mp 110-112° C., 60.1%

IR, 1842 (C(=O)—F) cm$^{-1}$; $[\alpha]^{24}$ = +33.6, c = 1, CH$_2$Cl$_2$.

(c) FMOC—Lys(BOC)—F: Mp 108-110° C., 63.9%

IR, 1846 (C(=O)—F) cm$^{-1}$; $[\alpha]^{23}$ = 2.0, c = 0.5, CH$_2$Cl$_2$;

(d) Z—Ala—F: Oil, 69%;

IR, 1840 (C(=O)—F) cm$^{-1}$; $[\alpha]^{24}$ = -7.1, c = 1, EtOAc;

(e) Z—Phe—F: Mp 81-83 °C., 61%;

-continued

IR, 1846 (C=O—F) cm$^{-1}$; $[\alpha]^{24}$ = -34.2, c = 1, EtOAc;

(f) FMOC—Asp(O-t-Bu)—F: Mp 72-74 °C., 67.5%

$[\alpha]^{24}$ = +3.8, c = 0.5, EtOAc.

Example 32

Examples of Racemization Tests. General Method for Coupling.

To 0.25 mmol of protected amino acid dissolved in 1 mL of solvent, 0.25 mmol of DIEA was added at 0° C. followed by 0.27 mmol of TFFH or another fluoroformamidinium salt and the mixture stirred at 0° C. for 5–10 min. There was then added 0.25 mmol of an ester.HCl or an amide and an equivalent amount of base (ester.HCl, 2 eq of base; amide, 1 eq of base). The reaction mixture was stirred at 0° C. for 1 h and at rt for 1 h. The mixture was diluted with EtOAc (15 mL) and washed with HCl (1M), NaHCO$_3$ (1M), saturated NaCl, and dried. Removal of solvent gave the peptide which was checked directly by HPLC or 200 MHz $^1$H NMR for racemization. The results are given below for each peptide.

TABLE I

Preparation of Z—Phg—Val—OMe[a]

| CR[b] | Solvent | Base | Yield (%) | DL % |
|---|---|---|---|---|
| TFFH | CH$_2$Cl$_2$ | DIEA | 80.0 | 1.1 |
|  | CH$_2$Cl$_2$ | TMP | 75.6 | <1 |
|  | DMF | DIEA | 83.1 | 3.6 |
|  | DMF | TMP | 71.2 | 1.6 |
| BTFFH | CH$_2$Cl$_2$ | DIEA | 82.4 | 1.1 |
|  | DMF | DIEA | 82.9 | 3.4 |
|  | DMF | TMP | 70.2 | 1.4 |
| DFIH | CH$_2$Cl$_2$ | DIEA | 69.9 | 1.3 |
|  | DMF | DIEA | 56.9 | 3.5 |

[a]Mp 138–140° C.
[b]Coupling reagent.

TABLE II

Preparation of Z—Phg—Pro—NH$_2$[a]

| CR | Solvent | Base | Yield (%) | DL % |
|---|---|---|---|---|
| TFFH | DMF | DIEA | 78.9 | 10.17 |
|  | DMF | TMP | 59.8 | 6.9 |
|  | CH$_2$Cl$_2$ | DIEA | 76.9 | 4.9 |
|  | CH$_2$Cl$_2$ | TMP | 53.8 | 0.32 |
|  | CH$_2$Cl$_2$ | DIEA/TMP | 86.3 | <0.1 |
| BTFFH | CH$_2$Cl$_2$ | DIEA | 78.6 | 4.3 |
|  | CH$_2$Cl$_2$ | DIEA/TMP | 82.4 | <0.1 |
| TCFH | DMF | DIEA | 67.8 | 12.91 |
|  | DMF | TMP | 45.4 | 5.43 |
|  | CH$_2$Cl$_2$ | DIEA | 78.7 | 6.1 |
|  | CH$_2$Cl$_2$ | TMP | 40.5 | 3.3 |
| TBFH | DMF | DIEA | 40 | 8.39 |
|  | DMF | TMP | 31.7 | 4.7 |
|  | CH$_2$Cl$_2$ | DIEA | 45 | 15.9 |
|  | CH$_2$Cl$_2$ | TMP | 38.1 | 20.7 |

TABLE II-continued

Preparation of Z—Phg—Pro—NH$_2$[a]

| CR | Solvent | Base | Yield (%) | DL % |
|---|---|---|---|---|
| DCIH | DMF | DIEA | 69.8 | 11.4 |
|  | DMF | TMP | 41.2 | 6.2 |

[a]Mp 89–92° C.; $[\alpha]_D^{23}$ = +54.5 (c = 1, EtOAc).

In order to establish that no racemization occurred during the preparation of Z-Phg-F via the fluoroformamidinium salts, a sample of the fluoride was coupled to proline amide in CH$_2$Cl$_2$ in the presence of collidine. HPLC analysis showed that less than 0.1% of the DL-isomer was formed, thus establishing that no racemization occurs during acid fluoride preparation.

TABLE III

Preparation of Fmoc—His—Pro—NH$_2$ from Fmoc—His(Trt)—OH

| Halo salt | Base | Solvent | Yield (%) | DL % |
|---|---|---|---|---|
| TFFH | DIEA | DMF | 78.21 | 8.16 |
|  | TMP | DMF | 71.8 | 6.4 |
| TCFH | DTEA | DMF | 67.8 | 29.2 |
|  | TMP | DMF | 45.4 | 25.5 |
| TBFH | DIEA | DMF | 40 | 51.75 |
|  | TMP | DMF | 31.7 | 31.33 |
| BTFFH | DIEA | DMF | 79.1 | 8.23 |
|  | TMP | DMF | 73.1 | 6.27 |
| DFIH | DIEA | DMF | 76.1 | 8.98 |
|  | TMP | DMF | 69.0 | 6.31 |
| TFFH | DIEA | CH$_2$Cl$_2$ | 80.1 | 4.9 |
|  | TMP | CH$_2$Cl$_2$ | 69.8 | 1.06 |
|  | DIEA/TMP (1:1) | CH$_2$Cl$_2$ | 83.4 | 0.46 |
| TCFH | DIEA | CH$_2$Cl$_2$ | 78.7 | 6.05 |
|  | TMP | CH$_2$Cl$_2$ | 60.8 | 3.3 |
| TBFH | DIEA | CH$_2$Cl$_2$ | 45.9 | 20.7 |
|  | TMP | CH$_2$Cl$_2$ | 38.1 | 15.9 |

TABLE IV

Preparation of Fmoc—His—Pro—NH$_2$ from Fmoc—His(Bum)—OH

| Salt | Base | Solvent | Yield (%) | DL % |
|---|---|---|---|---|
| TFFH | DIEA | DMF | 81.2 | 6.4 |
|  | TMP | DMF | 68.2 | 1.2 |
| TCFH | DIEA | DMF | 71.8 | 15.6 |
|  | TMP | DMF | 56.8 | 11.2 |
| TBFH | DIEA | DMF | 46.0 | 21.3 |
|  | TMP | DMF | 45.0 | 16.5 |
| BTFFH | DIEA | DMF | 83.2 | 6.9 |
|  | TMP | DMF | 68.7 | 1.3 |
| DFIH | DIEA | DMF | 76.2 | 6.7 |
|  | TMP | DMF | 60.2 | 1.6 |

In the tables hereinabove and hereinbelow, TCFH is tetramethylchoroformamidium hexaflurophosphate and TBFH is tetramethylbromoformamidinium hexafluorophosphate, TMP is 2, 4, 6-trimethylpyridine (collidine) DIEA is disopropyl ethylamine, NMM is N-methylmorpholine, Ps is proton sponge (1,8-bis (dimethylamino)napthalene), DCM is methylene chloride and ACN is acetonitrile.

From these results it is clear that coupling of trityl-protected histidine is difficult. Best results are obtained in $CH_2Cl_2$ using a 1:1 mixture of DIEA and collidine, the former for activation, the latter for coupling. In addition, the fluoroformamidinium salts are safer than the chloro and bromo analogs. Finally, BUM protection appears to be superior to trityl protection.

Example 33

Synthesis of FMOC-Val-F from TPFFH

A solution of 0.5 mmol of FMOC-Val-OH and 0.5 mmol of DIEA in 5 mL of $CH_2Cl_2$ under $N_2$ was treated with 0.6 mmol of TPFFH at room temperature and the reaction mixture was stirred for 2 h after which 10 mL of $CH_2Cl_2$ was added. The solution was washed with crushed ice, dried ($MgSO_4$) and the solvent removed to give a white solid which after recrystallization from $CH_2Cl_2$/hexane gave the acid fluoride as white crystals, mp 109–111° C., IR (KBr) 1842 $cm^{-1}$, in 68.7% yield.

Example 34

Use of TFFH in Peptide Coupling Reactions (1) Coupling of Z-Phe-Val-OH with H-Ala-OMe. To a solution of 0.25 mmol of Z-Phe-Val-OH (0.0995 g, 0.25 mmol), H-Ala-OMe.HCl (0.0487 g, 0.25 mmol) and 0.75 mmol of the chosen base in 1 mL of solvent ($CH_2Cl_2$ or DMF), cooled in an ice bath, there was added 0.3 mmol of TFFH (0.079 g), the reaction being followed by TLC using EtOAc/hexane (7:3). Complete reaction required 4–5 hrs. After completion of the reaction in the case of DMF the mixture was diluted with ethyl acetate and washed with 2N HCl, 1M $NaHCO_3$ and saturated NaCl, dried ($MgSO_4$), the solvent removed with a rotary evaporator and hexane added to give a white solid, mp 196–199° C. which was examined in the crude state by $^1H$ NMR analysis at 200 MHz or HPLC analysis (Table V). As noted the appropriate base and a lowered temperature is required for avoidance of racemization.

TABLE V

Racemization During Formation of Z—Phe—Val—Ala—OMe.

| Run | Base | mp of crude product | yield (%) | DL (%)[a] in DMF (HPLC) | DL (%)[b] in DMF ($^1H$ NMR) | DL (%)[a] in $CH_2Cl_2$ (HPLC) |
|---|---|---|---|---|---|---|
| 1 | DIEA | 195–199 | 72.3 | 24.76 | 25.6 | 2.7 |
| 2 | NMM | 196–199 | 74.5 | 20.85 | 21.9 | — |
| 3 | JMP | 198–201 | 67.4 | 5.8 | 6.2 | — |
| 4 | PS (at RT) | 194–198 | 75.6 | 7.7 | 8.2 | — |
| 5 | PS (at −30° C.) | 196–199 | 56.7 | 1.2 | <1 | — |

[a]Solvent system 40% $CH_3CN$/60% $H_2O$/0.1% TFA, f = 1, $\lambda_{214}$, $R_t$ 16.3 min (LLL-), 18.6 (LDL-).
[b]Methoxy peaks: LL-δ 3.75, LDL-δ 3.70.

Example 35

(2) Coupling of Z-Phg-OH with H-Val-OMe

To 0.25 mmol of Z-Phg-OH, 0.25 mmol H-Val-OMe.HCl and 0.75 mmol of the chosen base in 1–2 mL solvent (DMF or $CH_2Cl_2$) at ice bath temperature was added 0.37 mmol of TFFH. After completion of the reaction, in the case of DMF, the reaction mixture was diluted with ethyl acetate and washed with 1N HCl, 1M $NaHCO_3$, saturated NaCl, dried ($MgSO_4$), and after removal of solvent with a rotary evaporator the crude product was checked by $^1H$ NMR analysis at 200 MHz (Table VI).

TABLE VI

RACEMIZATION DURING FORMATION OF Z—Phg—Val—OMe

| Run | Base | Solvent | yield (%) | mp ° C. of crude product | DL (%)[a] |
|---|---|---|---|---|---|
| 1 | DIEA | DCM | 82 | 137–139 | 1.3 |
| 2 | DIEA | DMF | 80 | 136–138 | 3.6 |
| 3 | NMM | DMF | 81 | 136–138 | 2.8 |
| 4 | TMP | DMF | 82–3 | 136–138 | 1.62 |

[a]Methoxy peaks: LL-δ 3.63, DL- 3.72.

Example 36

Preparation of Z-Phg-Val-OMe via Two-Phase Coupling

To 0.5 mmol of Z-Phg-OH and 0.5 mmol of H-Val-OMe.HCl dissolved in a mixture of 10 mL of $CH_2Cl_2$ and 10 mL of water containing 3 mmol of $Na_2CO_3$ there was added with stirring at room temperature 0.75 mmol of TFFH. After half an hour TLC (70% EtOAc, 30% hexane) showed that only a trace of starting material remained. After one hour an excess of $CH_2Cl_2$ was added and the solution washed with $H_2O$ and NaCl and dried over $MgSO_4$. Removal of solvent gave the dipeptide in 70.4%. yield as a white solid, mp 140–141° C.; $^1H$ NMR ($CDCl_3$) δ0.9–1.01 dd, 6H, $2CH_3$), 2.1–2.3 (m, 1H, CH), 3.63 (s, 3H, $OCH_3$), 4.5 (m, 1H, CH), 5.1 (d, 2H, $CH_2O$, 5.3 (d, 1H, CH), 6.1–6.2 (d, 1H, NH), 7.2–7.5 (m, 5H, aryl). Examination of the -OMe region of the NMR spectrum (the DL-diastereomer has its methoxy peak at δ3.73) showed that only about 1.1% of the DL-isomer was present.

Example 37

Preparation of FMOC-Phe-Ala-OMe via Two-Phase Coupling

To 0.6 mmol of FMOC-Phe-F (prepared from TFFH) in 5 mL of $CH_2Cl_2$ there was added a mixture of H-Ala-OMe.HCl (0.5 mmol) and $Na_2CO_3$ (1.5 mmol) in 10 mL of $CH_2Cl_2$ and 5 mL of $H_2O$. The reaction mixture was stirred at room temperature for 30 min and then washed with 10% $KHSO_4$, 10% $NaHCO_3$, and NaCl, dried ($MgSO_4$), and the solvent removed with a rotary evaporator to give the dipeptide in 87.3% yield as a white solid, mp 166–168° C., $^1H$ NMR ($CDCl_3$) δ 1.3 (d, 3H, $CH_3$), 3.1 (m, 2H, $CH_2$), 3.73 (s, 3H, $OCH_3$), 4.3–4.5 (m, 5H; $CH_2$, 5CH), 5.5 (d, 1H, NH), 6.4 (d, 1H, NH), 7.1–7.9 (m, 13H, aryl). Examination of the NMR spectrum in the C-Me doublet region of the alanine unit (LL- δ1.3 d; DL-δ 1.2d) showed that less than 1% of the DL-form was present in the crude material.

Example 38

Preparation of FMOC-Phe-Ala-OMe via Direct Coupling with TFFH

To 0.5 mmol of FMOC-Phe-OH and 0.5 mmol of Ala-OMe.HCl dissolved in a mixture of10 mL of $CH_2Cl_2$ and 5 mL of $Na_2CO_3$ containing 1.5 mmol of $Na_2CO_3$ there was added a solution of TFFH (0.75 mmol) in 5 mL of $CH_2Cl_2$ and the reaction mixture was stirred at room temperature for 1 hr. An excess of $CH_2Cl_2$ was added and the organic layer was separated, washed with $H_2O$, NaCl and dried ($MgSO_4$). Removal of the solvent with a rotary evaporator gave in 87.3% yield the dipeptide as a white solid, mp 166–168° C.; $^1$H NMR (CDCl$_3$) same as described above. Examination of the $^1$H NMR at 200 MHz showed that less than 1% of the DL-form was present.

The same method was used to obtain an authentic sample of the DL-form, mp 162–164° C. For the C-Me doublets, the following data were obtained: DL-δ 1.25 d, 3H; LL-1.35 d. It is thus clear that there is no significant racemization during either the synthesis of FMOC-Phe-F from TFFH or during the in situ use of TFFH as a coupling reagent.

Example 39

Synthesis of Leucine Enkephalin in Solution via the two-Phase Method

To 0.5 mmol of H-Leu-O-t-Bu.HCl (0.112 g) and 0.5 mmol of FMOC-Phe-OH (0.189 g) in 10 mL of CH$_2$Cl$_2$ and 5 mL of 5% Na$_2$CO$_2$ which was being stirred at room temperature there was added 0.75 mmol of TFFH (0.198 g) in 5 mL of CH$_2$Cl$_2$. The stirring was continued for 1 hr. The organic layer was separated and washed with H$_2$O and saturated NaCl, dried over MgSO$_4$ and the solvent was removed with a rotary evaporator to give a white solid which was dissolved in 10 mL of CH$_2$Cl$_2$. The solution was used directly for deblocking by adding 7 mL of TAEA and allowing the mixture to stand for 15 min after which it was washed with saturated NaCl (2×10 mL) and phosphate buffer of pH 5.5 (3×15 mL). After drying over MgSO$_4$, removing the CH$_2$Cl$_2$ and adding fresh CH$_2$Cl$_2$ (10 mL) and 5 mL of Na$_2$CO$_3$ (5%), there was finally added 0.5 mmole of FMOC-Gly-OH followed by 0.75 mmole of TFFH. The work-up described above was repeated until the protected pentapeptide FMOC-Tyr(O-t-Bu)-Gly-Gly-Phe-Leu-O-t-Bu had been obtained in a yield of 60.7% as a white solid (0.265 g). The protected pentapeptide was dissolved in 10 mL of CH$_2$Cl$_2$ and 7 mL of TAEA added. After stirring at room temperature for 30 min the solution was washed with saturated NaCl (2×10 mL) and then with pH 5.5 phosphate buffer (3×15 mL), dried and the solvent was removed. After silica gel chromatography (EtOAc/hexane/HOAc) (7:3:0.1) the pure peptide was dissolved in 50% TFA/CH$_2$Cl$_2$ (15 mL). After stirring at room temperature for 2 hrs solvent and TFA were removed in vacuo with a water aspirator. Ether was added at −20° C. in order to precipitate the free peptide as a white solid (0.16 g, 48.1%). The crude sample was injected into an HPLC system using a Delta Pak Column (5μ, C$_{18}$, 100 Å, 3.9×150 mm); λ 220 nm; chart speed=0.3, f=1; gradient solvent system as follows:

| Time (min) | ACN | H$_2$O 0.1% TFA |
|---|---|---|
| 0 | 10 | 90 |
| 20 | 90 | 10 |
| 21 | 10 | 90 |

The leucine enkephalin showed R$_t$ 15.5 min and was 93.6% pure. Co-injection with an authentic sample which was prepared from FMOC-AA-OPFP esters gave a single HPLC peak.

Example 40

Synthesis of Leucine Enkephalin by Solid Phase Synthesis (a) Automatic Solid Phase Synthesis on a Millipore 9050 Instrument. The synthesis was executed on an FMOC-Leu-PEG-PS resin under the following conditions: Amt: 0.6 g of starting resin; coupling time: 30 min; deblocking time: 15 min; preactivation time: 7 min. Reagents: 5 eq of FMOC-AA-OH; 5 eq of TFFH; DMF solvent. After release from the resin and removal of the t-Bu group by treatment with TFA for 2 hrs at room temperature, evaporation and cooling to −30° C. followed by addition of ether gave the pentapeptide salt as a yellowish white solid in 53% yield. HPLC analysis showed a major peak for leucine enkephalin at R$_t$ 15.05 min (88.5% purity).

(b) Manual Solid Phase Synthesis. The synthesis was carried out on 0.2 g of the same resin described above. Conditions: deblocking time: 15 min; coupling time: 1 hr. Reagents: 3 eqs of FMOC-AA-OH; 4 eqs of DIEA; 4 eqs of TFFH. After normal deblocking and release from the resin precipitation gave the peptide salt as a white solid in 56% yield. Co-injection with an authentic sample of leucine enkephalin (R$_t$ 15.5 min, Delta Pak Column, 5μ) proved the identity of the product.

Example 41

Synthesis of Leucine Enkephalin via TPCFH

The method of the previous example was followed except that 0.2 g of FMOC-Leu-PEG-PS resin (0.21 mmol/g) was used with 10-min deblocking time and 20-min coupling time (preactivation 2–3 min). The peptide had a purity of 81.1%.

Example 42

Synthesis of Leucine Enkephalin via TPFFH

The method followed that of Example 41 and gave a product of 84.1% purity.

Example 43

Comparison of Solid Phase Reactivity in the Coupling Step for TXFH, X=F, Cl, Br

A sample of FMOC-Leu-PEG-PS (0.18 mmol/g) was deblocked by 20% piperidine in DMF for 15 min in a plastic syringe attached to a vacuum manifold. After deblocking, the resin was washed with three 10-mL portions of DMF, three 10-mL portions of CH$_2$Cl$_2$, two 10-mL portions of DMF and finally treated with 5 eqs of FMOC-Val-OH, 5 eqs of the appropriate coupling reagent TXFH (X=F, Cl, Br) and 10 eqs of DIEA in 1 mL of DMF. The preactivation time was 2–5 min. At intervals 5–15 mg of resin was removed, washed, deblocked with 2 mL of 20% piperidine in DMF and the extent of coupling determined by UV analysis at 300.5 nm. Results are listed in Table VIII.

TABLE VIII

| PERCENT REACTION AT VARIOUS TIMES FOR THE COUPLING OF FMOC—Val—OH TO LEUCINE ATTACHED TO PEG—PS | | | | |
|---|---|---|---|---|
| Time (min) | TFFH | TCFH | TBFH | TPFFH |
| 2 | 76.9 | 65 | 60.5 | 74.5 |
| 4 | 90.1 | 66.7 | 65.6 | 84.6 |
| 6 | 91.2 | 76.7 | 70.1 | 90.1 |
| 8 | 94.3 | 81.9 | — | 100 |
| 10 | 100 | 86.5 | 79.5 | 99.1 |
| 15 | 100 | 91.6 | 84.2 | 100 |
| 20 | 100 | 91 | 86.3 | 100 |
| 30 | 98.2 | 97.3 | 91.6 | 98.6 |

These results confirm that the fluoroformamidinium reagents lead to more rapid coupling (after 10–15 min. coupling has finished for both fluoro reagents whereas it is only 86.5–91.6% and 79.5–84.2% complete for the chloro and bromo analogs). This agrees with the expectation that the latter two reagents lead to oxazolone formation from the intermediate acid chloride and acid bromide, respectively.

Example 46

Synthesis of Prothrombin via TFFH via Solid Phase Synthesis (Millipore 9050)

The synthesis was carried out in the normal manner described hereinabove using 0.6 g of FMOC-PAL[1]-PEG[2]-PS resin (0.25 mmol/g) with the following protocol:

(1) 1 mmol FMOC amino acid.
(2) 1 mmol of TFFH.
(3) 2 mmols of DIEA (0.6M solution in DMF, 3 mL total volume).
(4) Coupling time: 30 min.
(5) Deprotection time: 5–7 min.
(6) Preactivation time: 5–7 min.

The crude peptide showed a purity of 95% (HPLC) and on co-injection with an authentic sample eluted at the same retention time.

Synthesis of Alamethicin Acid via Solid Phase Synthesis (Millipore 9050). The synthesis was performed on 0.5 g of FMOC-Phe-PEG-PS (0.19 mmol/g) as described above and gave a crude peptide showing a purity of 90% (HPLC).

[1]PAL is a peptide amide linker sold by Millipore.
[2]PEG-PS is polyethylene glycol polystyrene resin.

Example 45

Synthesis of ACP (H-Val-Gln-Ala-Ala-Ile-Asp-Tyr-Ile-Asn-Gly-OH) using TFFH

The synthesis was carried out as described hereinabove normally on the Millipore 9050 instrument using the following conditions:

1) Fmoc-Gly-PEG-PS (0.2 mmol eq/gm).
2) 5 eq of Fmoc-AA-OH, 5 eq of TFFH, 10 eq of DIEA, 1–2 mL DMF, conc. –0.3M.
3) preactivation time: 5–7 min.
4) coupling time: 30 min.
5) Deblocking time: 7 min, 20% piperidine/DMF.
6) Yield: 85%; purity (HPLC): 92.75.

Example 46

Coupling Via TFFH in the Absence and Presence of an Additive

A mixture of 0.125 mmol of TFFH, 0.125 mmol of HOAt, 0.125 mmol of base and 0.5 mL of DMF was stirred at rt for 2 min and then the mixture was added at 0° C. to 0.125 mmol of an acid, 0.125 mmol of an ester.HCl or 0.125 mmol of an amide, along with 0.32 mmol of TMP for an ester salt or 0.18 mmol of TMP for a free amide. The reaction mixture was stirred at 0° C. for 1 hour, at room temperature for 1 hour, and then worked up as usual.

| Peptide | % LDL- (without additive) | % LDL- (with additive) |
|---|---|---|
| I. Z—Phe—Val—Ala—OMe | 23 | 1.98[a] <0.1[b] |
| II. Z—Gly—Phe—Val—OMe | 25 | 8.1[a] <0.1[b] |
| III. Z—Phe—Val—Pro—NH$_2$ | 46.2 | 9.3[a] 0.65[b] |
| IV. Z—Gly—Phe—Pro—NH$_2$ | — | 5.3[a] 0.5[b] |
| V. Z—Phe—Val—Pro—OH | 47.1 | — <0.1[b] |

[a]DIEA used for activation (TFPH/HOAt) and TMP for coupling.
[b]TMP used for both activation (TFFH/HOAt) and coupling.

These results demonstrate that HOAt represents a useful additive for use with TFFH in those cases, especially segment condensations, where TFFH alone is not satisfactory. For solid phase syntheses this modification is not necessary in general although it could be advantageous in the case of α-phenylglycine or histidine.

Other examples are indicated in the table below:

Solid Phase Coupling of Fmoc—Val—OH with H—Ile—PEG—PS in DMF and Comparison with Coupling of Preformed Fmoc—Val—F

| CR | Base | Time | Extent of Coupling[a] |
|---|---|---|---|
| TFFH | DIEA | 2 | 76.9 |
| | | 4 | 90.1 |
| | | 6 | 91.2 |
| | | 8 | 94.3 |
| | | 10 | 100 |
| | | 15 | 100 |
| | | 20 | 100 |
| Preformed acid fluoride | DIEA | 2 | 70.9 |
| | | 4 | 78.9 |
| | | 6 | 89.6 |
| | | 10 | 99.3 |
| | | 15 | 98.8 |
| | | 20 | 100 |
| TFFH | TMP | 4 | 16.7 |
| | | 6 | 20 |
| | | 10 | 26.5 |
| | | 20 | 32 |
| Preformed acid fluoride | TMP | 2 | 62.8 |
| | | 4 | 74.9 |
| | | 6 | 84.8 |
| | | 10 | 89.2 |
| | | 15 | 98.8 |
| | | 20 | 100 |
| TFFH | PS | 5 | 57.6 |
| | | 10 | 83.6 |
| | | 15 | 81.5 |
| | | 20 | 85.7 |
| | | 30 | 97.5 |
| Preformed acid fluoride | PS | 2 | 69.2 |
| | | 6 | 84.9 |
| | | 10 | 91.3 |
| | | 15 | 98.7 |
| | | 20 | 100 |
| Preformed acid fluoride | 2,6-bis(TMS)-pyridine | 2 | 42.3 |
| | | 4 | 50.4 |
| | | 6 | 52.6 |
| | | 10 | 63.1 |
| | | 15 | 85.9 |
| | | 20 | 84.3 |
| TFFH | DIEA-TMP (1:1) | 2 | 68.9 |
| | | 5 | 79.6 |
| | | 10 | ~100 |
| | | 15 | 98.39 |
| | | 20 | –100 |
| | | 30 | –99.8 |

[a]UV analysis.

From these results it is clear that collidine is less effective as an activating agent than DIEA but a 1:1 mixture of the two bases is nearly as effective as DIEA alone. This allows collidine, which is less likely to promote racemization, to be used for the coupling step. It also appears that in the presence of DIEA alone TFFH is slightly more reactive than preformed acid fluoride. This suggests that during the activation of TFFH by DIEA there is formed an intermediate which not only reacts with fluoride ion to give acid fluoride, but also reacts, and reacts more readily than the acid fluoride, with the amino group on the resin.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for forming a peptide bond between a first amino acid having a free amino group and a protected carboxy group and a second amino acid or between a peptide having a free amino group and a protected carboxy group with a second amino acid which comprises (a) reacting the second amino acid of the formula:

with a fluoroformamidinium salt of the formula:

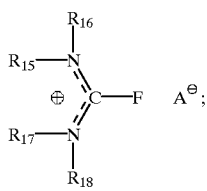

and (b) reacting the product of (a) with the first amino acid or peptide wherein AA is an amino acid residue;

BLK is a N-amino protecting group;

X is absent or is a protecting group on the side chain of the second amino acid;

$R_{15}, R_{16}, R_{17}$ and $R_{18}$ are independently lower alkyl, aryl, aryl lower alkyl, cycloalkyl, cycloalkyl lower alkyl or $R_{15}$ and $R_{16}$ taken together with the nitrogen atom to which they are attached form a 5- or 6-membered ring containing a nitrogen ring atom and 4 or 5 carbon ring atoms and up to total of 10 carbon atoms, or $R_{17}$ and $R_{18}$ taken together with the nitrogen atom to which they are attached form a 5- or 6-membered ring containing a nitrogen ring atom and 4–5 ring carbon atoms and up to a total of 10 carbon atoms or $R_{16}$ and $R_{17}$ taken together with the nitrogen atoms to which they are attached and the carbon atom attached to said nitrogen atoms form a 5- or 6-membered ring containing 2 nitrogen ring atoms and 3–4 ring carbon atoms and up to a total of 10 carbon atoms and A is a counterion.

2. The process of claim 1 wherein the (a) second amino acid of the formula

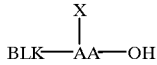

is reacted with the fluoroformamidinium salt and (b) the product of (a) is reacted with the first amino acid or peptide in the presence of said fluoroformamidinium salt, wherein the fluoroformamidinium salt has the formula:

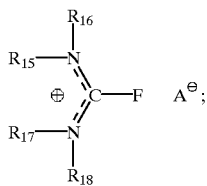

wherein $R_{15}, R_{16}, R_{17}$ and $R_{18}$ are independently lower alkyl, aryl, aryl lower alkyl, cycloalkyl, cycloalkyl lower alkyl or $R_{15}$ and $R_{16}$ taken together with the nitrogen atom to which they are attached form a 5- or 6-membered ring containing a nitrogen ring atom and 4 or 5 carbon ring atoms and up to a total of 10 carbon atoms, or $R_{17}$ and $R_{18}$ taken together with the nitrogen atom to which they are attached form a 5- or 6-membered ring containing a nitrogen ring atom and 4–5 ring carbon atoms and up to a total of 10 carbon atoms or $R_{16}$ and $R_{17}$ taken together with the nitrogen atoms to which they are attached and the carbon atom attached to said nitrogen atoms form a 5- or 6-membered ring containing 2 nitrogen ring atoms and 3–4 ring carbon atoms and up to total of 10 carbon atoms and A is a counterion.

3. A process for forming a peptide bond between a first amino acid having a free amino group and a second amino acid or between a peptide having a free amino group and a second amino acid which comprises reacting the first amino acid or peptide with an amino acid fluoride of the formula

in the presence of a fluoroformamidinium salt having the formula:

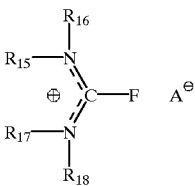

wherein

BLK is a N-amino protecting group, AA is an amino acid residue, X is absent or is - or a protecting group on the side chain of the amino acid, $R_{15}, R_{16}, R_{17}$ and $R_{18}$ are independently lower alkyl, aryl, aryl lower alkyl, cycloalkyl, cycloalkyl lower alkyl or $R_{15}$ and $R_{16}$ taken together with the nitrogen atom to which they are attached form a 5- or 6-membered ring containing a nitrogen ring atom and 4 or 5 carbon ring atoms and up to a total of 10 carbon atoms, or $R_{17}$ and $R_{18}$ taken together with the nitrogen atom to which they are attached form a 5- or 6-membered ring containing a nitrogen ring atom and 4–5 ring carbon atoms and up to a total of 10 carbon atoms or $R_{16}$ and $R_{17}$ taken together with the nitrogen atoms to which they are attached and the carbon atom attached to said nitrogen atoms form a 5- or 6-membered ring containing 2 nitrogen ring atoms and 3–4 ring carbon atoms and up to a total of 10 carbon atoms and A is a counterion.

4. The process according to claims 1, 2 or 3 wherein $R_{15}, R_{16}, R_{17}$ and $R_{18}$ are independently lower alkyl or aryl or $R_{15}$ and $R_{16}$ taken together with the nitrogen atom to which they are attached form a ring containing a nitrogen ring atom or $R_{18}$ and $R_{17}$ taken together with the nitrogen atom to which they are attached form a ring containing a nitrogen ring atom or $R_{16}$ and $R_{17}$ taken together with the nitrogen atoms to which they are attached and the carbon atom attached to said nitrogen atoms form a 5- or 6-membered ring containing 2 ring nitrogen atoms.

5. The process of any one of claims 1–3 wherein $R_{15}$, $R_{16}$ and $R_{17}$ are lower alkyl and $R_{18}$ is lower alkyl or aryl.

6. The process of any one of claims 1–3 wherein $R_{15}$ and $R_{16}$ are the same.

7. The process of any one of claims 1–3 wherein $R_{15}$, $R_{16}$ and $R_{17}$ are the same.

8. The process of any one of claims 1–3 wherein $R_{15}$, $R_{16}$, $R_{17}$ and $R_{18}$ are the same.

9. The process of any one of claims 1–3 wherein lower alkyl is alkyl containing 1–3 carbon atoms.

10. The process of any one of claims 1–3 wherein lower alkyl is methyl and aryl is phenyl.

11. The process of any one of claims 1–3 wherein $R_{15}$, $R_{16}$ and $R_{17}$ are all methyl and $R_{18}$ is methyl or phenyl.

12. The process of any one of claims 1–3 wherein $R_{15}$ and $R_{16}$ taken together with the nitrogen atom to which they are attached form a piperidine or pyrrolidine.

13. The process of any one of claims 1–3 wherein $R_{17}$, and $R_{18}$ taken together with the nitrogen atom to which they are attached form a piperidine or pyrazolidine.

14. The process of any one of claims 1–3 wherein $R_{15}$ and $R_{16}$ taken together with the nitrogen atom to which they are attached and $R_{17}$ and $R_{18}$ taken together with the nitrogen atom to which they are attached each form a piperidine or pyrrolidine.

15. The process of any one of claims 1–3 wherein $R_{16}$ and $R_{17}$ taken together with the carbon atom to which they are attached form an imidazolidine or hexahydropyrimidine.

16. The process of any one of claims 1–3 wherein the

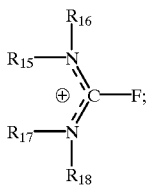

is tetramethyl fluoroformamidinium, trimethylphenyl fluoroformamidinium, bis (tetramethylene) fluoroformamidinium or 1,3-dimethyl-2-fluoroimidizolium.

17. The process of any one of claims 1–3 wherein HOAt is additionally present.

18. The process of claims 1 or 3 wherein AA is an α-amino acid residue.

19. The process of claim 18 wherein AA is an amino acid residue selected from the group consisting of glycine, alanine, leucine, isoleucine, proline, hydroxyproline, phenylalanine, tyrosine, methionine, norleucine, serine, threonine, cystine, cysteine, tyrosine, aspartic acid, glutamic acid, asparagine, glutamine, lysine, arginine, hydroxy lysine, ornithine, histidine and tryptophan.

20. The process of claims 1 or 3 wherein BLK is CBZ, Bspoc, Bsmoc, FMOC, BOC AIMOC, BIMOC, Dbd-TMOC, AOC, ADOC, Mch, Bpoc, Ddz, HCO, TFA, TEOC, MOZ, Tac, Benz[e]indene-1-methoxy carbonyl, Benz-[e]-indene-3-methoxy carbonyl, piperidine-oxycarbonyl, phthaloyl, Azoc, Poc, Fac, Nps, Dts, formyl, acetyl or trifluoroacetyl.

21. The process of claim 19 wherein BLK is Bspoc, Bsmoc, FMOC, BPoc, BOC, CBZ, formyl or trifluoroacetyl.

22. The process of any one of claims 1–3 wherein additionally present is 1-hydroxybenzotriazole or a compound of the formula:

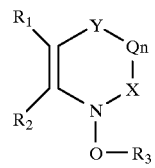

II or an N-oxide thereof, or a salt thereof wherein $R_1$ and $R_2$ taken together with the carbon atoms to which they are attached form a heteroaryl ring wherein said heteroaryl ring is an oxygen, sulfur, or nitrogen containing heteroaromatic containing from 3 and up to a total of 13 ring carbon atoms, said heteroaryl may be unsubstituted or substituted with lower alkyl or an electron donating group;

Y is O, $NR_4$, or $CR_4R_5$;

$R_5$ is independently hydrogen or lower alkyl;

X is $CR_6R_7$ or $NR_6$;

$R_6$ and $R_7$ are independently hydrogen or lower alkyl; or $R_6$ and $R_7$ taken together with the carbon atom to which they are bonded optionally represent an oxo group or when n=0, $R_4$ and $R_6$ taken together may form a bond between the nitrogen or carbon atom of Y and the nitrogen or carbon atom of X;

Q is —$C(R_8R_9)$— or —$NR_8$—;

when n is 1, $R_4$ and $R_8$ taken together may form a bond between the ring carbon or nitrogen atom of Q and the ring carbon or nitrogen atom of $R_8$;

n is 0, 1, or 2;

$R_3$ is hydrogen; and $R_8$ and $R_9$ are independently hydrogen or lower alkyl or $R_7$ and $R_8$, taken together with the carbon atoms to which they are attached, form an aryl ring.

23. PyFLOP.

* * * * *

UNITED STATES PATENT AND TRADEMARK OFFICE
CERTIFICATE OF CORRECTION

PATENT NO. : 6,040,422

DATED : March 21, 2000

INVENTOR(S) : Louis A. Carpino, et al.

It is certified that error appears in the above-identified patent and that said Letters Patent is hereby corrected as shown below:

On The Title Page, [56] References Cited, OTHER PUBLICATIONS: "2220-2202"

should read --2200-2202--

Column 2, Line 38: "prepare" should read --prepared--

Column 18, Line 65: "acide" should read --acid--

Column 31, Line 40: "bromophosphoium" should read --bromophosphorium--

Column 32, Line 3: Insert Title --Synthesis of Acid Fluorides--

Column 34, Line 32: "DTEA" should read --DIEA--

Column 34, Line 1: "tetramethylchoroformamidium" should read- -tetramethylchloroformamidinium--

Column 35, Line 56: "LL" should read --LLL--

UNITED STATES PATENT AND TRADEMARK OFFICE
CERTIFICATE OF CORRECTION

PATENT NO. : 6,040,422
DATED : March 21, 2000
INVENTOR(S) : Louis A. Carpino, et al.

It is certified that error appears in the above-identified patent and that said Letters Patent is hereby corrected as shown below:

Column 39, Line 59: "TFPH" should read --TFFH--

Column 44, Line 44, Claim 22: "(R8R9" should read --(R R )--

Signed and Sealed this

Fifteenth Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO.    : 6,040,422
DATED         : March 21, 2000
INVENTOR(S)   : Louis A. Carpino et al.

It is certified that error appears in the above-identified patent and that said Letters Patent is hereby corrected as shown below:

<u>Column 1,</u>
Line 5, insert the following, -- This invention was made with Government support under Grant No. NIH GM 09706 awarded by the National Institutes of Health and Grant No. NSF CHE 8609176 awarded by the National Science Foundation. The Government has certain rights in the invention. --

Signed and Sealed this

Twenty-ninth Day of January, 2002

Attest:

JAMES E. ROGAN
*Attesting Officer*     *Director of the United States Patent and Trademark Office*